United States Patent
Meyer

(10) Patent No.: US 6,267,988 B1
(45) Date of Patent: Jul. 31, 2001

(54) COMPOSITION AND METHOD FOR INDUCING SATIETY

(76) Inventor: James H. Meyer, 2210 La Mesa Dr., Santa Monica, CA (US) 90402

( * ) Notice: Subject to any disclaimer, the term of this patent is extended or adjusted under 35 U.S.C. 154(b) by 0 days.

(21) Appl. No.: 09/081,045

(22) Filed: May 19, 1998

Related U.S. Application Data

(63) Continuation of application No. 08/263,349, filed on Jun. 21, 1994, now Pat. No. 5,753,253, which is a continuation-in-part of application No. 07/889,710, filed on May 28, 1992, now Pat. No. 5,322,697.

(51) Int. Cl.$^7$ ........................................ A61K 9/14
(52) U.S. Cl. .................. 424/489; 424/439; 424/494; 424/496; 424/497; 514/772.3; 514/781; 514/951
(58) Field of Search .................... 424/439, 464, 424/489, 490, 494, 496, 497, 484, 485, 486, 488, 487

(56) References Cited

U.S. PATENT DOCUMENTS

| | | | |
|---|---|---|---|
| 5,273,754 | * 12/1993 | Mann | 424/440 |
| 5,290,560 | * 3/1994 | Autant et al. | 424/438 |
| 5,401,512 | * 3/1995 | Rhodes et al. | 424/458 |

FOREIGN PATENT DOCUMENTS

87/03198    6/1987   (WO) .

OTHER PUBLICATIONS

Meyer, J.H., et al. Chemical specificities and intestinal distributions of nutrient–driven satiety. *Am J. Physiol.* 275 (Regulatory Integrative Comp. Physiol. 44) R1293–R1307, 1998.

Raybould, Helen E., et al. Inhibition of gastric emptying in response to intestinal lipid is dependent on chylomicron formation . . . *Am J. Physiol.* 274 (Regulatory Integrative Comp. Physiol. 43) R1834–R1838, 1998.

Meyer, J.H., et al. Length of intestinal contact on nutrient–driven satiety. *Am J. Physiol.* 275 (Regulatory Integrative Comp. Physiol. 44) R1308–R1319, 1998.

Meyer, J.H., et al. Role of small intestine in caloric compensations to oil premeals in rats. *Am J. Physiol.* 275 (Regulatory Integrative Comp. Physiol. 44) R1320–R1333, 1998.

Matzinger, D., et al. The role of long chain fatty acids in regulating food intake and cholecystokinin release in humans, *Gut 2000. 46,* 688–693, 2000.

\* cited by examiner

*Primary Examiner*—James M. Spear
(74) *Attorney, Agent, or Firm*—Fulbright & Jaworski, LLP

(57) ABSTRACT

A composition and method for the control of appetite having food grade nutrients as the active ingredients, and a pharmaceutically acceptable delivery agent, formulated so that the active ingredient is released predominantly in the ileum. The active ingredient may include sugars, fatty acids, polypeptides, and amino acids. The delivery agent may be a pH sensitive coating, a cellulosic polymer coating or a diazotized polymer. The composition may be formulated into pellets of between 1 and 3 mm with a density of around 1.0. The composition may be administered with a liquid as a slurry, or it may be administered in a tablet form. The composition may be used in conjunction with any weight loss or weight maintenance program.

11 Claims, 23 Drawing Sheets

COMPOSITION AND METHOD FOR INDUCING SATIETY

This is a continuation application of U.S. patent application Ser. No. 08/263,349, filed Jun. 21, 1994, now U.S. Pat. No. 5,753,253, which is a continuation-in-part application of U.S. patent application Ser. No. 07/889,710, filed May 28, 1992, now U.S. Pat. No. 5,322,697.

BACKGROUND OF THE INVENTION

1. Field of the Invention

This invention relates to a composition and method for controlling appetite in humans. More particularly, the invention concerns the targeting of nutrients for the ileum to induce satiety in a human being.

2. Related Technology

A major class of weight control agents are drugs which act on the central nervous system (CNS) to suppress appetite. One major subclass of CNS appetite suppressant drugs interacts with cathecolaminergic receptors in the brainstem. These include controlled drugs such as amphetamine, phenmetrazine, and diethylproprion, and over-the-counter drugs such as phenylpropanolamine. Manizidol is another CNS active drug which, although not a catecholamine, activates the central nervous system. Each of these agents have potential for addiction and, at doses which effectively reduce appetite, i.e., suppress food intake by 20–30%, they induce significant CNS side effects, such as nervousness, loss of concentration, and insomnia. Another subclass of CNS active appetite control drugs interferes with serotonergic systems. D-fenfluramine, for example, releases and depletes brain serotonin, but it causes sedation at appetite suppressant levels, and it may precipitate depression upon its withdrawal. Fluoxetine is an inhibitor of serotonin re-uptake in the brainstem. However, at effective appetite control doses, Fluoxetine often causes nausea and asthenia, i.e., weakness, lassitude.

Another major class of weight control agents are drugs which promote malabsorption of nutrients through suppression of digestive enzymes. One agent in this category is Acarbose, a bacterial inhibitor of amylase and brushborder glycosidases. Another is tetrahydrolipostatin, a fungal inhibitor of lipases. These agents work by preventing digestion of carbohydrates and/or fats, thus creating an effective reduction in the number of calories absorbed, despite continued consumption. One drawback is that virtually complete inhibition of the respective enzymes must be maintained throughout the digestive period, a situation that can be rarely achieved. Thus, Acarbose was shown to be ineffective in humans, and tetrahydrolipostatin was shown to reduce human absorption of fat by only 30%. A second major drawback to this approach is that subjects taking these agents develop hyperphagia for other foodstuffs. For example, subjects taking tetrahydrolipostatin will consume more carbohydrate to compensate for the loss of fat absorption. Thus, the loss of calories from malabsorption is compensated by an increased intake of food, especially of foodstuffs of a different class.

A third class of weight control agents are noncaloric, non-nutritive dietary substitutes, like saccharin or Nutrasweet, sugar substitutes, and sucrose polyester, a fat substitute. These agents, while not absorbed, provide a taste and/or texture like the nutrient for which they are substituted. The disadvantage of these substitutes is that persons develop a hyperphagia to compensate for the reduction of calories by the substitution. With sucrose polyester, a non-digestible lipid, fat soluble, enterohepatically circulated vitamins partition into the unabsorbed polyester and are lost from the body, a potential problem which can also occur with tetrahydrolipostatin.

Thermogenic drugs are also sometimes used. The catecholamine drugs discussed above have some thermogenic activity, in addition to their suppression of appetite. Thyroid hormone is also commonly used.

Semi-starvation diets are universally effective in short term weight loss, but regain of weight after resumption of less restricted diets is the rule. Long term use of semi starvation diets is nutritionally unsound because of the development of multiple deficiencies of essential nutrients.

Surgical devices have also been employed to control appetite. Intragastric balloons have been placed endoscopically according to the theory that they increase the amount of gastric distension and thus augment satiety responses. However, they have been discontinued because, while they were not shown to be any better than restricted diets in promoting weight loss, their long term use was associated with severe side effects such as gastric ulceration and migration of the balloons into the small intestine resulting in intestinal obstructions.

Patients with morbid obesity (body mass index>29 kg/m2, about 3% of the overweight population) are often encouraged to undergo bariatric surgery because, as a class, they suffer from more than four times the incidence of diabetes, cardiovascular disease, uterine and breast cancer, degenerative joint disease, and social stigmatization. Ileojejunal bypass, the first such surgery undertaken 30 years ago, has now been abandoned because of severe side effects such as poor subsequent malnutrition, fatal cirrhosis or renal failure. Biliopancreatic by-pass, gastric by-pass, and gastric partitioning (stapling) are the current procedures, but the long term side effects have not yet been determined.

BRIEF DESCRIPTION OF THE INVENTION

It is an object of the present invention to provide a composition and method for controlling appetite in animals that avoids the disadvantages and side-effects associated with the known compounds, compositions, and methods.

Accordingly, there is provided a composition comprising: a pharmaceutically acceptable satiety agent which may include at least one active ingredient selected from the group consisting of food grade nutrients (natural foodstuffs), and a pharmaceutically acceptable delivery agent, formulated to spread of the active ingredients over a length of the intestine. There is also provided according to the invention a composition comprising: a pharmaceutically acceptable satiety agent which may include at least one active ingredient selected from the group consisting of food grade nutrients (natural foodstuffs), and a pharmaceutically acceptable delivery agent, formulated for release of the active ingredients in the ileum. According to a further embodiment of the invention, the composition may be formulated for release predominantly in the ileum. Food grade nutrients may include but are not limited to sugars, free fatty acids, polypeptides, amino acids and suitable foods that are precursors thereto. According to one embodiment of the invention, the active ingredient is selected from the group consisting of sugars, free fatty acids, phenylalanine polypeptides, and amino acids. According to another embodiment, the active ingredient may include monomeric sugars, such as glucose and xylose. Furthermore, chemical derivatives or chemical analogs of "sensed" natural foodstuffs may be used in place of, or together with, natural foodstuffs to enhance the potency of the satiety response, through more favorable solubility, buffered ph, absorption, affinity to nutrient sensors in the intestine, or some combination of these properties. For example, docecylsulfate is an analog of decanoate, a natural foodstuff. Sodium decanoate and sodium dodecylsulfate are preferred active ingredients. Pharmaceutically acceptable delivery agents include ion exchange resins and enteric coatings, such as pH sensitive polymers, diazotized polymers, and cellulosic polymers.

There is further provided a method for controlling appetite comprising targeting selected satiety agents to specific portions of the intestines. There is also provided a method for controlling appetite comprising spreading a selected satiety agent over a length of intestine. There is further provided a method for controlling appetite comprising a) selecting an active ingredient from the group consisting of food grade nutrients, b) selecting an enteric coating from the group consisting of pH sensitive polymers, diazotized polymers, and cellulosic polymers, c) encapsulating the selected active ingredient with the selected enteric coating into particles of between 1 and 3 millimeters in diameter with a density of between 0.5 and 2.0, and d) orally administering an effective dosage to an animal. According to yet another aspect of the invention, the method further comprises releasing the active ingredient predominantly in the ileum. Once release begins, it occurs over the length of the ileum.

The present invention is a synthesis of several discoveries which have been pioneered by the inventor.

The intestines are responsible for a portion of satiety feedback. However, the inventor has found that the small intestine is much more sensitive to nutrient stimulus in triggering satiety than is the large intestine. In addition, it was discovered that the intensity of a satiety response to nutrients in the intestines is proportional to the length of bowel over which the nutrients are absorbed. Finally, the inventor demonstrated for the first time that artificially retarding the rate of absorption of a nutrient in the ileum, which under natural conditions is immediately and entirely absorbed as soon as it enters the ileum, magnifies the potency of the nutrient in eliciting an ileum initiated satiety response. The term "artificially" as used in the context of this invention means actively and purposefully influenced by, or controlled by, man.

Thus, the present invention is a novel and unobvious integration of the aforementioned discoveries of powerful satiety responses to nutrients in the ileum, the summation of sensory response with length of bowel contacted by the nutrient stimulus and, in turn, the enhancement of nutrient potency by artificially retarding its rate of absorption and thus extending its length of intestinal contact to trigger more sensors. Accordingly, a preferred embodiment of the present invention takes advantage of all three of these discoveries through the slow release from enteric coated, multiparticulate dosage forms which release small amounts of nutrients at different dissolution times to create a spread of nutrients and achieve the highest release and absorption profiles in ileum, the site of the most effective satiety sensation. A release profile simply reflects the amount of nutrient released by a delivery agent at any point along the digestive tract. An absorption profile of a specific nutrient reflects the absorption of that nutrient at any point along the digestive tract.

The enteric coated nutrient may be administered as tablets or as a slurry drink, with or between meals. The dosage form may be designed to promote ileal release and spread at the time of the next scheduled feeding. In this fashion, a very small amount of nutrient, less than 5 g for example, may produce a marked satiety effect.

The appetite control composition of the invention may be used as an adjunct to a weight loss program to reduce increased hunger or craving for food during the forced restriction in caloric intake. Alternatively, the composition of the invention may be used as a direct weight-loss-maintenance device, effective by virtue of the ability of the composition to reduce food intake by about 40%; or as an adjunct to a restricted weight-loss-maintenance diet, effective by virtue of the ability of the composition to induce satiety.

DETAILED DESCRIPTION OF THE INVENTION

One of the primary feedback mechanisms influencing appetite and satiety is the presence of nutrients in the gastrointestinal tract. Although gastric distension, i.e., stomach stretch, is considered by most researchers to be the single most important satiety signal, some researchers have suggested that the presence of nutrients in the intestines may contribute to satiety feedback. However, the preconception is so strong that gastric distension is paramount, that most researchers argue that intestinal nutrients act only through the slowing of gastric emptying of food, thereby indirectly promoting gastric distension, and thus, even more indirectly, contributing to satiety.

This invention is based in part on the inventor's discovery that the absorption of nutrients from the intestines triggers a powerful satiety feedback, independent of gastric distension.

Additionally, the inventor has also found that the distal intestine is more sensitive to nutrients than the proximal intestine, such that the same amount of nutrient will produce more satiety in the ileum than it would have in the jejunum. Again, this effect was discovered to occur independently of gastric or intestinal stretch.

Some of these studies were made using a modified sham-fed rat model. Using this model, the inventor was able to show the efficiency of satiating nutrients on infusion into distal small intestine, to ascertain the approximate range of infused dose-response, and to study interactions between the satiating effects of two or more compounds. Other studies involved natural free-feeding rats, implanted with infusion catheters. In these studies, it was shown that targeting the pharmaceutical delivery of nutrients to the ileum will produce a higher and a more consistent reduction ratio than delivery of nutrients to the jejunum.

Studies were also made in dogs with biliary fistulas. It was discovered that food intake in these dogs was significantly reduced when bile was diverted from the jejunum so as to increase the amount of unabsorbed, but digested fat reaching the ileum. The idea that satiety was more potently stimulated from ileum than from jejunum was further supported by studies in other dogs equipped with chronically implanted perfusion catheters to allow perfusion selectively of jejunum and of ileum. In these dogs, a fat-containing solution of sugar and peptides inhibited food intake significantly more potently when perfused into ileum than when perfused into jejunum. In further studies in still other dogs with pancreatic fistulas, diverting endogenous pancreatic enzymes from their normal entry into duodenum to enter, instead, at mid intestine reduced food intake in eleven free-feeding dogs over eight day feeding periods reproducibly to as low as 70% of control. Displacing the digestion of food from proximal to distal bowel, when digestive enzymes were diverted there, exposed ileal sensors to much higher concentrations of nutrients than normal, resulting in an augmented satiety response. In these experiments, ileal volume flows were not increased. Yet these dogs had normal to slow rates of gastrointestinal transit so that this result was not a matter of gastric or ileal distension or aversive conditioning.

The invention also encompasses the discovery that the intensity of a biological response to the presence of nutrients in the small intestine is dependent upon the intensity of the stimulus per unit length of bowel and the length of bowel contacted. Specifically, it was observed that the magnitude of pancreatic secretion and gastric emptying responses to nutrients in the ileum varied in proportion to the length of bowel contacted by the nutrient. At maximum nutrient concentrations, the response became simply proportional to the length of bowel contacted by the stimulus.

For example, hydrogen ions, which are known to stimulate pancreatic secretion, were found to be potent even at a low initial concentration if they are bound (i.e., prevented from release and absorption) to weak acid anions that carry them downstream or are slowed from diffusion out of the bowel lumen by increased luminal viscosity and/or by encapsulation within the interstices of liver particles.

In another study, the inventor found that infusing 1.1 mmoles/min of glucose into the duodenum of dogs produced about half as much inhibition of gastric emptying as infusing 0.25 mmoles/min simultaneously into the 1st, 2nd, 3rd, and 4th quarters of the small intestine. This study demonstrated that the spread of glucose over the small intestine would augment its stimulated response, i.e., inhibition of gastric emptying.

The inventor hypothesized that if absorption of particular satiety inducing nutrients could be reduced or delayed, and length of small intestinal mucosal contact increased, the satiety response could be significantly magnified.

Normally, however, nutrients are rapidly absorbed and quickly disappear from the intestinal lumen because of active transport carriers or facilitated diffusion. The inventor has discovered, however, that increasing luminal viscosity and delaying availability, by the encapsulation of satiety inducing nutrients within enteric coated multi-particulates, the nutrients could be selectively delivered to and spread out over the more sensitive ileum.

By entericly coating nutrients in small spheres of different sizes (i.e., "multi particle dosage forms"), the satiety inducing nutrients may be delivered to and spread out over the ileum. First, the transit of spheres from stomach to intestine and along small intestine varies with sphere size and density. Therefore, the individual spheres spread out along small intestine as they move into and through it. Second, the rate of dissolution of the enteric coating varies to some degree from sphere to sphere. This variation further increases the length of small intestine over which the nutrient is released. Normally, nutrients would be absorbed rapidly once they enter small intestine, so that they usually are almost entirely absorbed before mid intestine. Since the enteric coatings on the spheres prevent the release of the nutrients until the coating dissolves, the distance over which a small amount of nutrient can be spread without being absorbed depends on (a) the transit characteristics of the spheres and (b) the rate of dissolution of the coating. Thus, a multi-particle dosage form is a means of achieving a long spread of contact between nutrient and intestinal mucosa. Furthermore, if release is programmed to occur in distal small intestine (ileum), higher luminal viscosity there will also serve to retard absorption and to further spread the released nutrient.

Since satiety feedback from distal small bowel (ileum) is more intense per amount of sensed nutrient than from proximal bowel (jejunum), timing the release (i.e., time to coating dissolution) to predominate in ileum will also enhance the satiety response per amount of agent ingested. Thus, both the spread and predominant site of delivery (ileum) will maximize the effect, so that a small amount of released nutrient will be sensed as though it were a large amount, creating a high satiating effect.

Finally, if the agent is also ingested so that its release in the ileum coincides with the time of the next scheduled feeding, the useful satiety response will be maximized. The time of emptying from the stomach is generally 2 hours. The time of intestinal transit is 2–4 hours. Thus, if the dosage form is taken with a meal, a medium time of gastric emptying of 2 hours, followed by dissolution of the enteric coating after reaching ileum in another 2–4 hours will maximally enhance satiety 4–6 hours later, at the time of the next meal.

This system is designed to maximize satiety feedback from normal intestinal sensors by small amounts of nutrients or nutrient derivatives, in essence, to "fool" body sensors which are not usually in contact with nutrients unless very large amounts are ingested. One significant advantage of this approach is one of minimal or no toxicity.

STUDY 1

Figure 1:
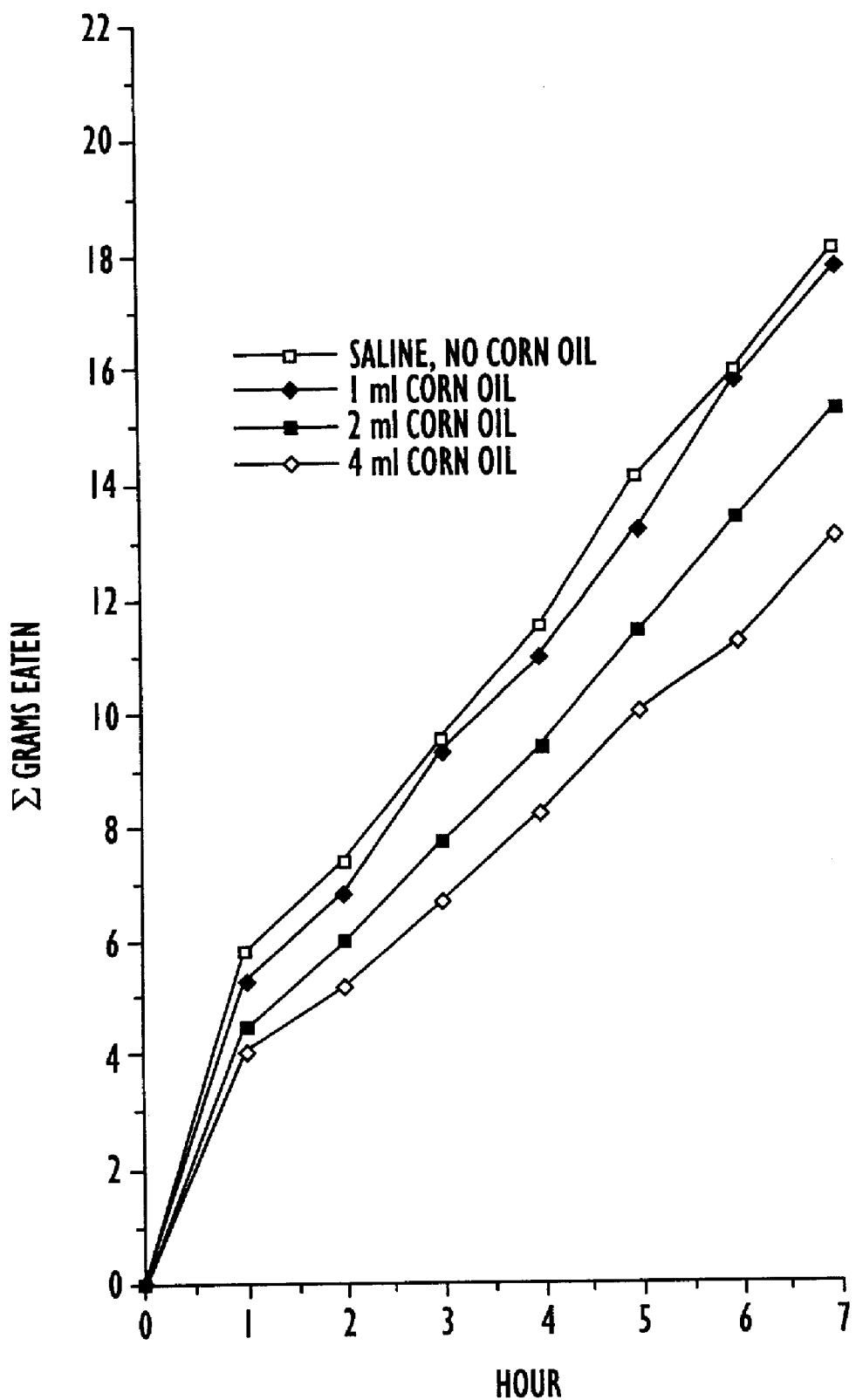
FIG. 1 is a graphic representation of the results of Study 1 described below.

Monkeys, pigs, humans, and rats are able to sense calories instilled into the stomach and compensate for these by reducing subsequent caloric intake, a quantitative response which constitutes "satiety". In this study, rats were trained to eat daily for 0900 to 1600 h, following brief orogastric intubation. Food consumption was measured hourly for 7 h after preloads of 4 ml were instilled into the rats' stomachs by orogastric intubation; the 4 ml preloads consisted of mixtures of 0.15M NaCl and corn oil, such that 0, 1, 2, and 4 ml of corn oil were given just prior to the 7 h feeding period. FIG. 1 illustrates that the rates reduced their food intakes in proportion to the calories instilled in the oil preloads; significant ($p<0.0001$), dose-related compensatory reductions were already evident by 1 h and continued over the entire 7 h feeding period.

Figure 2:
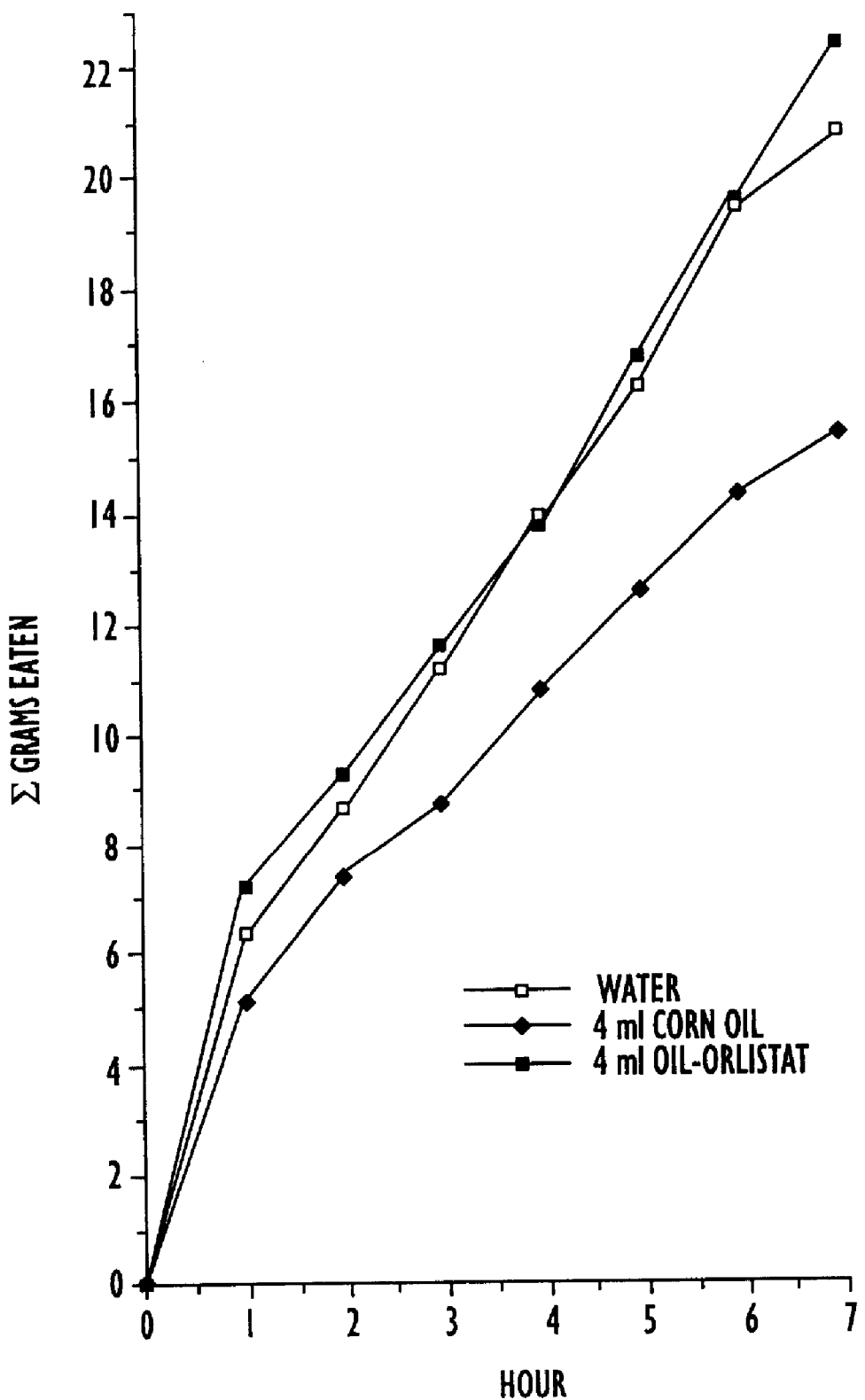
FIG. 2 is a second graphic representation of the results of Study 1 described below.

In 15 of these rats, the study was repeated with preloads of 4 ml of saline (null control), 4 ml of corn oil (positive control) or 4 ml of corn oil to which the specific lipase inhibitor, Orlistat (F. Hofmann LaRoche) was added (13.3 mg/g of oil). The lipase inhibitor completely abolished the suppression of subsequent food intake by the corn oil preload (FIG. 2); that is, the 4 ml of oil without the inhibitor significantly reduced food intake (when compared with the saline control ($p<0.001$), whereas the oil+ Orlistat did not inhibit subsequent food intake any more than the preload of non-caloric saline.

Figure 3:
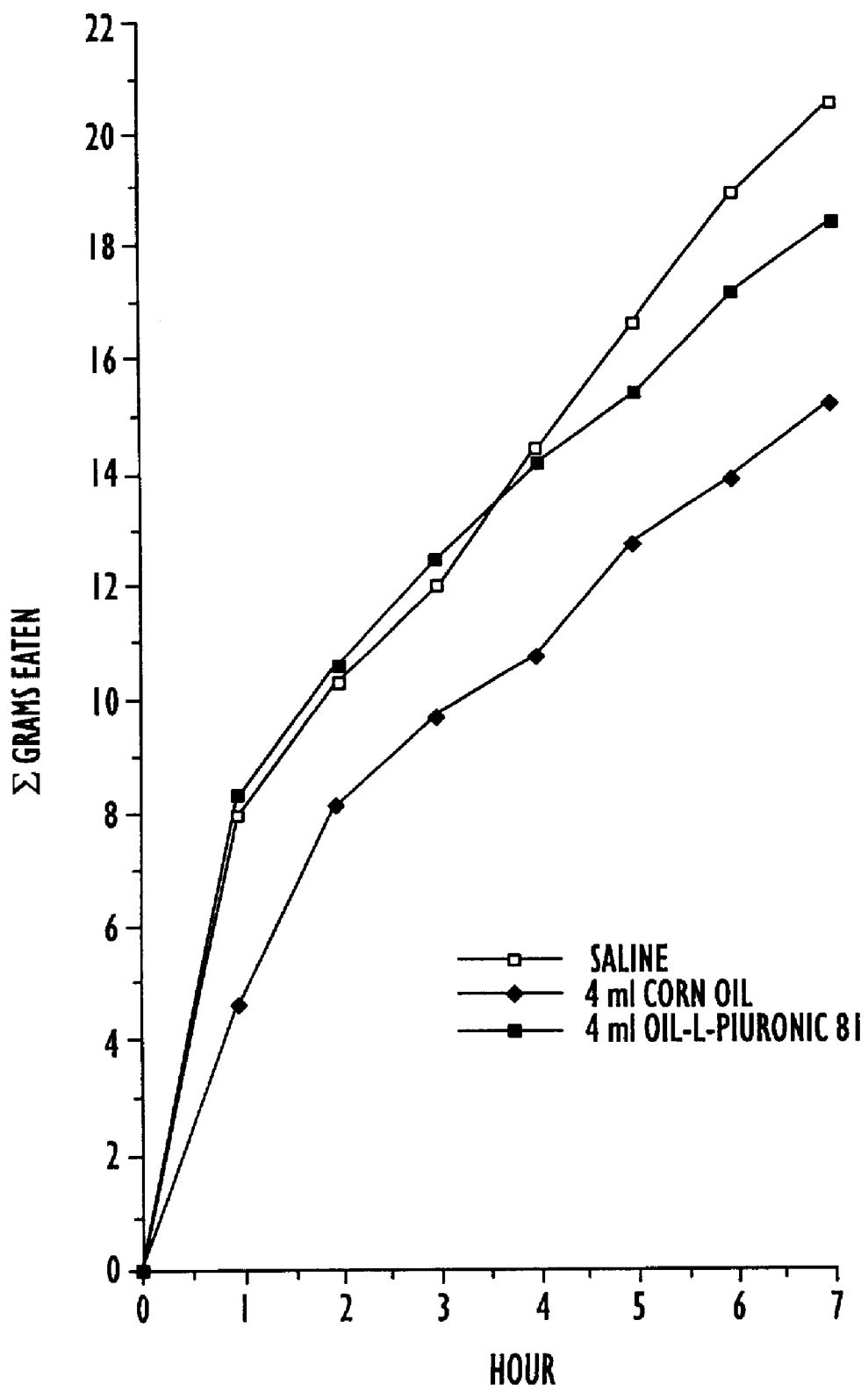
FIG. 3 is a third graphic representation of the results of Study 1 described below.

A similar experiment is depicted in FIG. 3 in the same 15 rats. Here, the rats were fed preloads of saline, corn oil, or corn oil plus L-pluronic acid, 81 (27.7 mg/g). L-pluronic 81 is a known inhibitor of intestinal transport of fat: when present in dietary fat, it allows the digestive products of fat to be absorbed by absorptive cells but blocks the formation of chylomicrons by which fatty acids, longer than 10 carbons, are transported out of the absorptive cell into intestinal lymph. The L-pluronic acid completely abolished the satiety response to the corn oil; that is, the oil. without the inhibitor suppressed food intake ($p.<0.001$, compared to the saline preload), but food intake after the oil with the L-pluronic acid was no different than after the saline.

These experiments demonstrate two important principles: (1) the effectiveness of ingested calories from oil in suppressing food intake depends on the hydrolysis of oil to free fatty acids, a response blocked by, Orlistat (in related experiments inhibition of lipolysis by the Orlistat was; confirmed), and (2) the satiation from the oil preloads did not originate in the stomach but arose from sensations generated after oil reached small intestine. This conclusion can be drawn from the experiments with L-pluronic acid 81, which is known to be a specific inhibitor of chylomicron transport (again, an action confirmed in other experiments by the inventor). Since the L-pluronic acid does not affect gastric digestion or intracolonic digestion and absorption, but only small intestinal transport, these experiments localize the satiating effect of the oil preloads to the small intestine and/or to systemic signals activated by oil after its absorption from small intestine.

STUDY 2

The sham-fed rat is a traditional model by which satiety signals from intestinal nutrients has been studied. In this model, rats are prepared with chronic, gastrocutaneous fistulae by surgically implanting a closable metal cannula into the stomach. In addition, a polyethylene perfusion catheter is placed chronically with its distal end in the duodenal lumen and its proximal end coming out from a subcutaneous tunnel at the back of the neck. After recovery from surgery, rats are trained to drink, while immobilized in a restraint cage, from a bottle containing a solution of pleasant tasting, nutrient. All solution imbibed enters the stomach and drains immediately out the opened gastric cannula into a pan. Thus, the stomach is never filled, the nutrient never reaches the small intestine, and the rats' drinking is relatively uninhibited, continuing for long periods of time. During this period of sham feeding, saline (null control) or various doses of nutrients can be infused by pump through the perfusion catheter into the duodenum. By measuring the milliliters of nutrient drunk during 90 min of sham feeding, the investigator can determine whether particular nutrients, in various doses, inhibit sham feeding in comparison with the saline, null control. Such inhibition has been regarded as a "satiety" response.

The inventor has modified this preparation by adding a second perfusing catheter with its distal end at midgut (55 cm from the pylorus) and its proximal end exiting from the back of the neck. When various doses of nutrients are infused through the proximal catheter into the duodenum, the nutrients have access to and may contact the whole small intestinal length; because of this potentially extensive access, nutrients so infused into duodenum may inhibit sham feeding, but the sites in the intestine! from which the "satiety" signal is generated cannot be determined. When nutrients are infused into the more distal catheter at midgut, they have access to only the distal half of the intestinal length; inhibition of sham feeding observed during perfusions at midgut would thus confirm the existence of feedback signals in distal small bowel and/or colon.

This model was used by the inventor: (1) to screen at variety of compounds for satiating effects; (2) to confirm efficacy of satiating nutrients on infusion into distal small intestine; (3) to ascertain the approximate range of infused dose-response; and (4) to study interactions between the satiating effects of two or more nutrient compounds.

Figure 4:
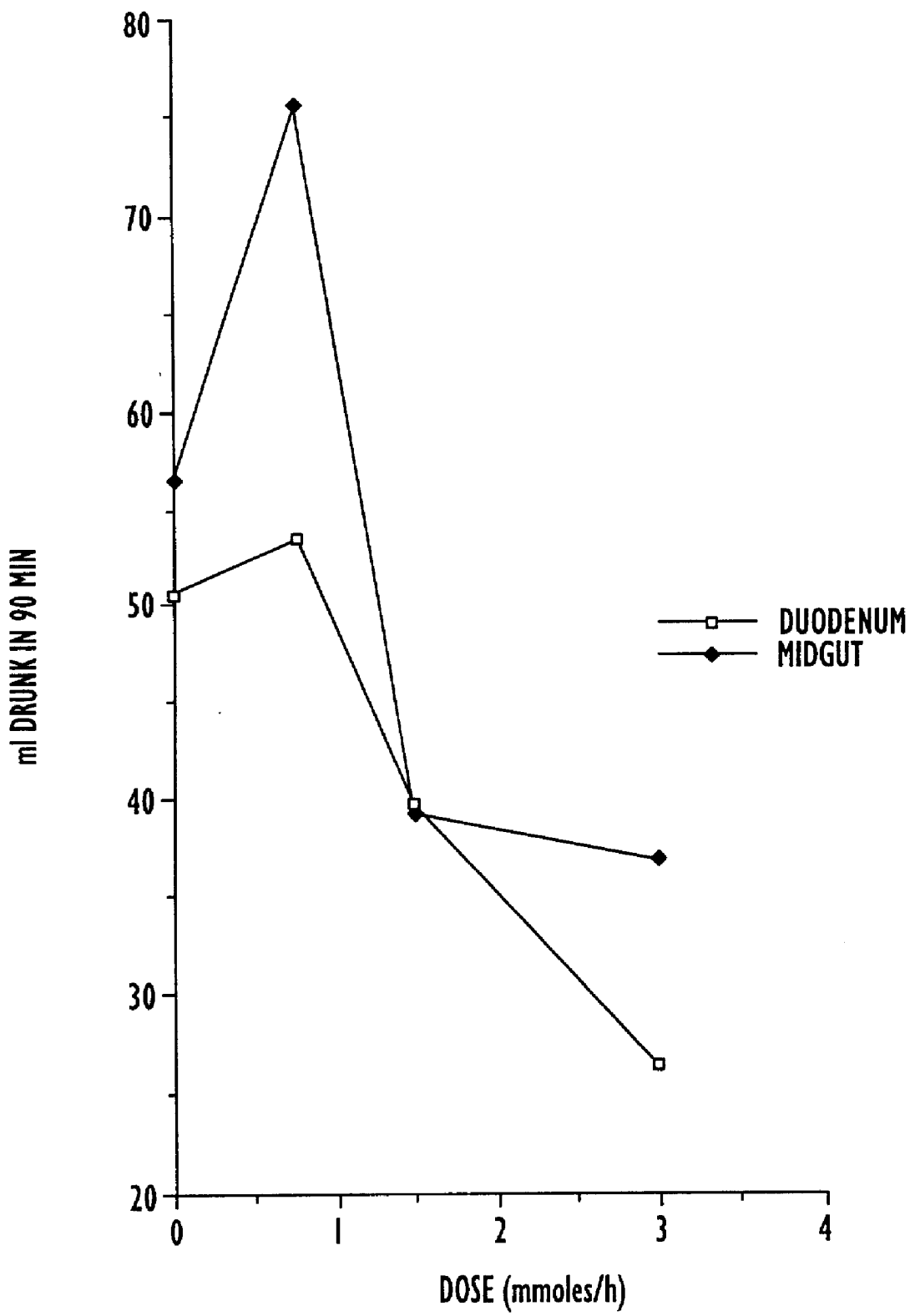
FIG. 4 is a graphic representation of the results of Study 2A described below.

Study 2A (Amino Acids):

The inventor infused L-phenylalanine at varied concentrations but fixed volume flows into duodenum and into midgut. He has confirmed a significantly dose-responsive ($p<0.001$) inhibition of sham feeding when L-phenylalanine was infused into midgut (FIG. 4). Infusion of the same range of doses into proximal small intestine produced more variable results which did not achieve statistical significance. The responses to the distal infusions were greater.

Confirmation of a satiety response to L-phenylalanine raised the question as to whether all amino acids are capable of provoking satiety. The ability of various L-amino acids to inhibit sham feeding in rats was studied by infusing them singly into the duodenum at the highest effective dose previously observed for L-phenylalanine. Responses to each individual amino acid were compared to responses during the saline control and, as well, to responses during infusion of phenylalanine (Table 1). Not all amino acids were effective; thus of the amino acids tested to date, alanine, leucine, and arginine were ineffective, while tryptophan, as well as phenylalanine, was effective. This observation indicates that not all amino acid congeners are active. The spectrum of activity among amino acids observed to date (i.e., aromatic amino acids) is similar to that previously described for (a) stimulation of pancreatic secretion (dog) and (b) inhibition of gastric emptying (man).

Figure 5:
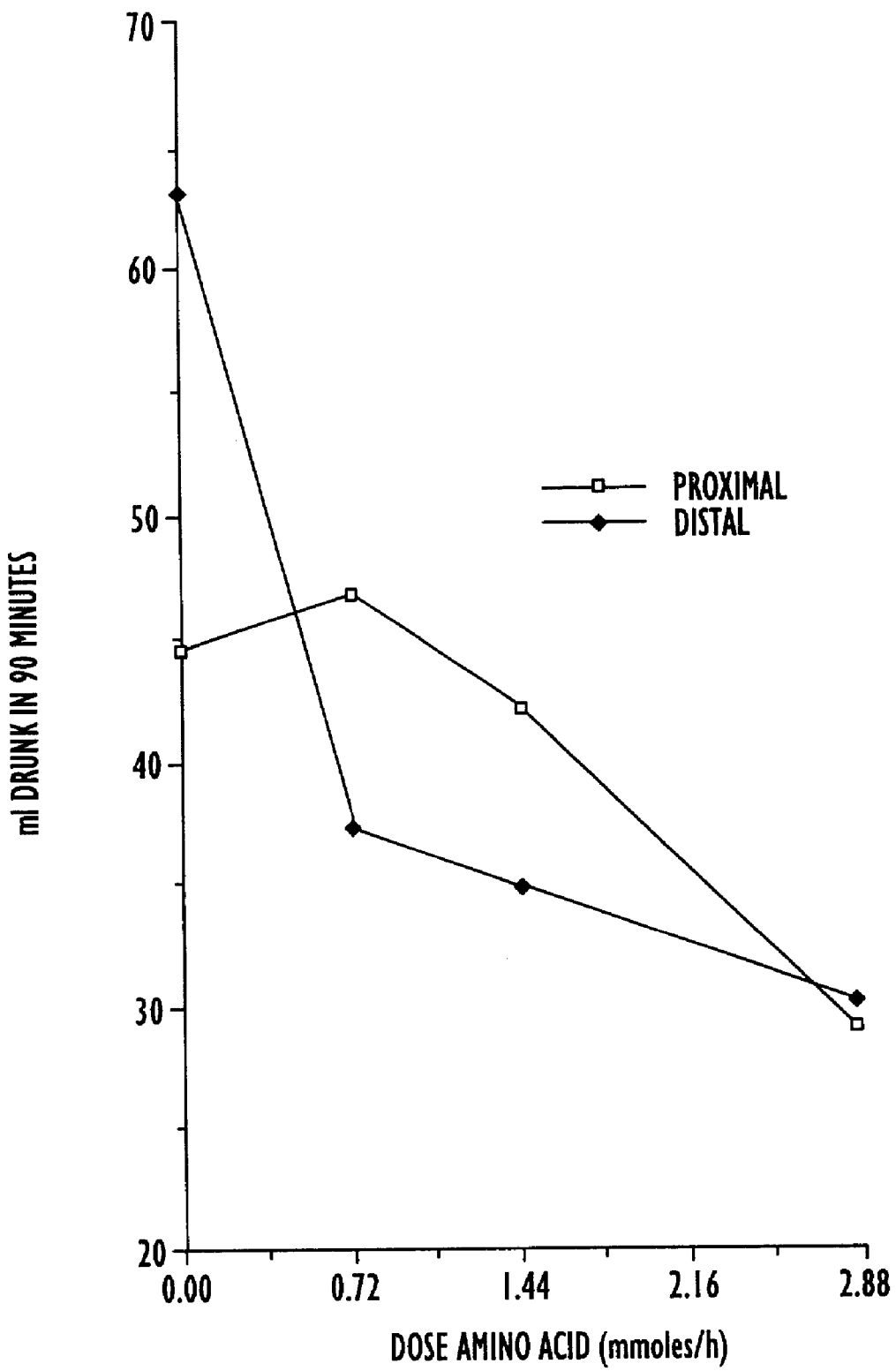
FIG. 5 is a second graphic representation of the results of Study 2A described below.

A binary mixture of L-phenylalanine (180 mM) and L-tryptophan (60 mM) was infused at varied volume flow (3–12 ml/h) into duodenum and midgut (FIG. 5). The doses infused were thus the same as previously with the L-phenylalanine alone (at fixed volume flow, varied concentrations; and the results were similar: the mixture significantly ($p<0.01$) and more profoundly inhibited sham feeding when infused into midgut, while results were more varied and statistically insignificant during perfusion into duodenum. A similar dose-response relationship was generated with midgut infusion of the binary mixture at fixed concentration, varied flow as with the phenylalanine alone at varied concentration, fixed flow. These observations indicate (1) that the inhibition of sham feeding over the doses utilized is responsive to load (g/h) infused independent of concentration and (2) that the responses to active amino acids within a mixture are additive.

Figure 6A:
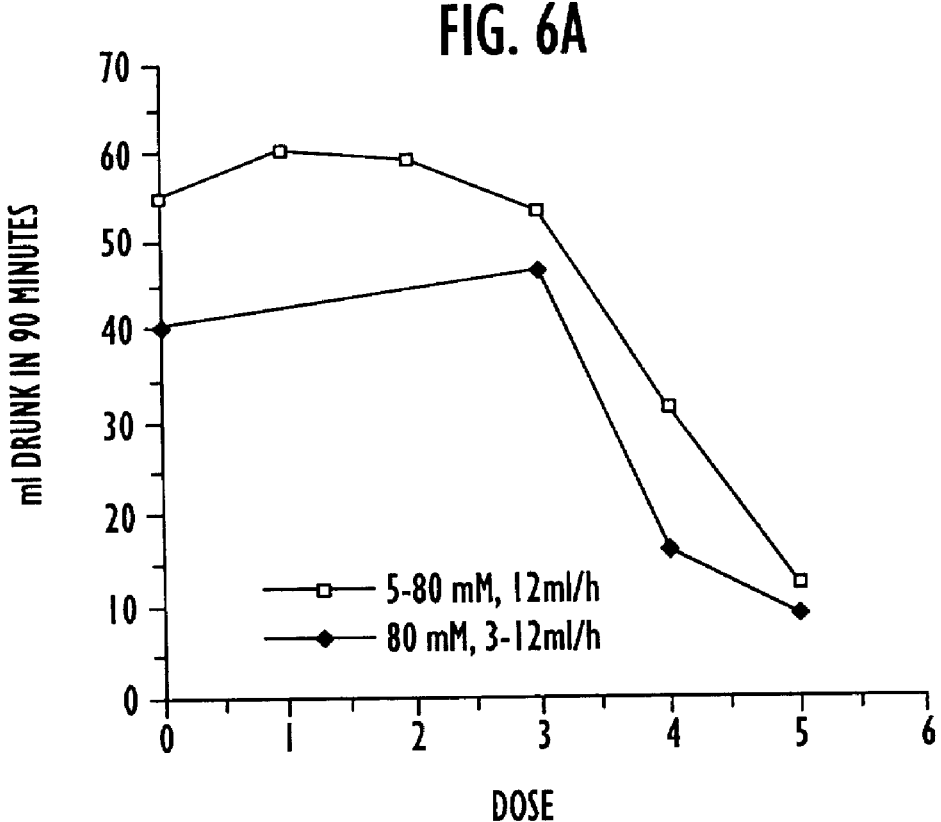
FIG. 6a is a graphic representation of the results of Study 2B described below.
Figure 6B:
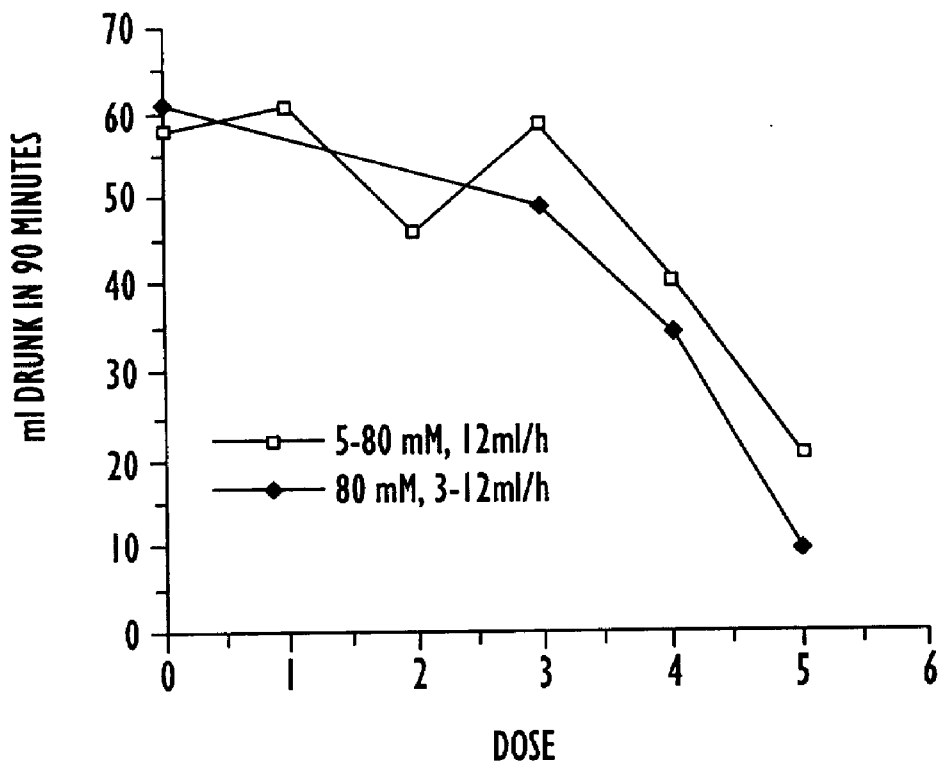
FIG. 6b is a second graphic representation of the results of Study 2B described below.

Study 2B (Fatty Acids):

The inventor infused oleic acid at pH 7 as mixed micelles with sodium taurocholate and monolein (in a 2:1 molar ratio with the latter), a mixture similar to that released during natural lipolysis. Whether infused into the duodenum or midgut, whether at fixed concentration, varied flow or at varied concentration, fixed flow (FIGS. 6a and 6b), the oleate monolein inhibited sham feeding in a load dependent fashion (p.<01), so that sham feeding was about 80% inhibited at the highest load (0.966 mmoles/h).

The inventor has tested four fatty acids for potency (Table 2). In addition to oleic acid, dodecanoic acid (as a pH 8.2 sodium soap) was found to be significantly ($p<0.01$) potent, but neither decanoate soap (pH 7.4) or octanoate soap (pH 7) were effective.

Figure 7A:
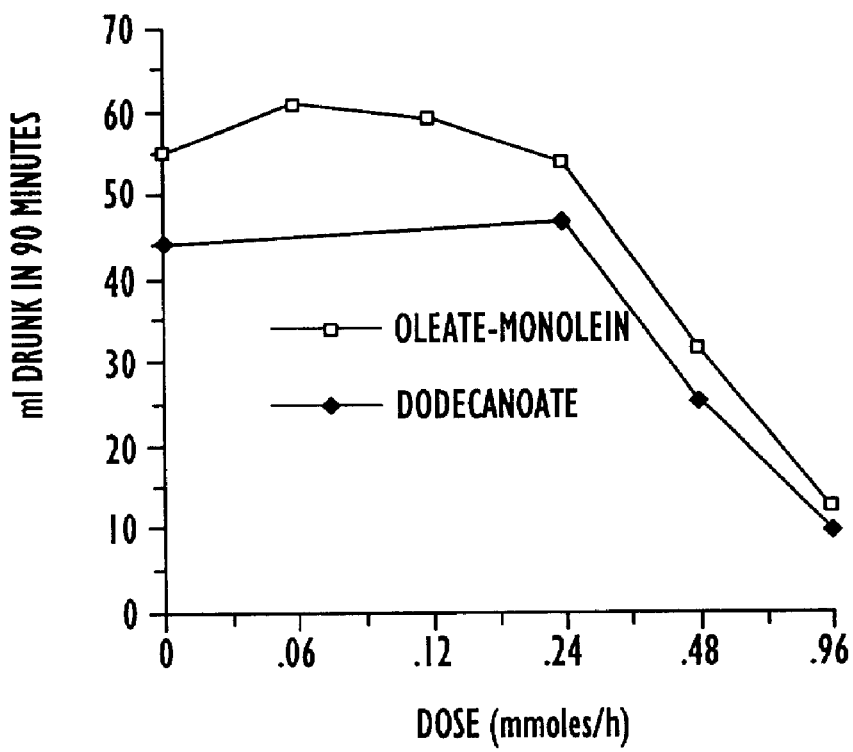
FIG. 7a is a third graphic representation of the results of Study 2B described below.
Figure 7B:
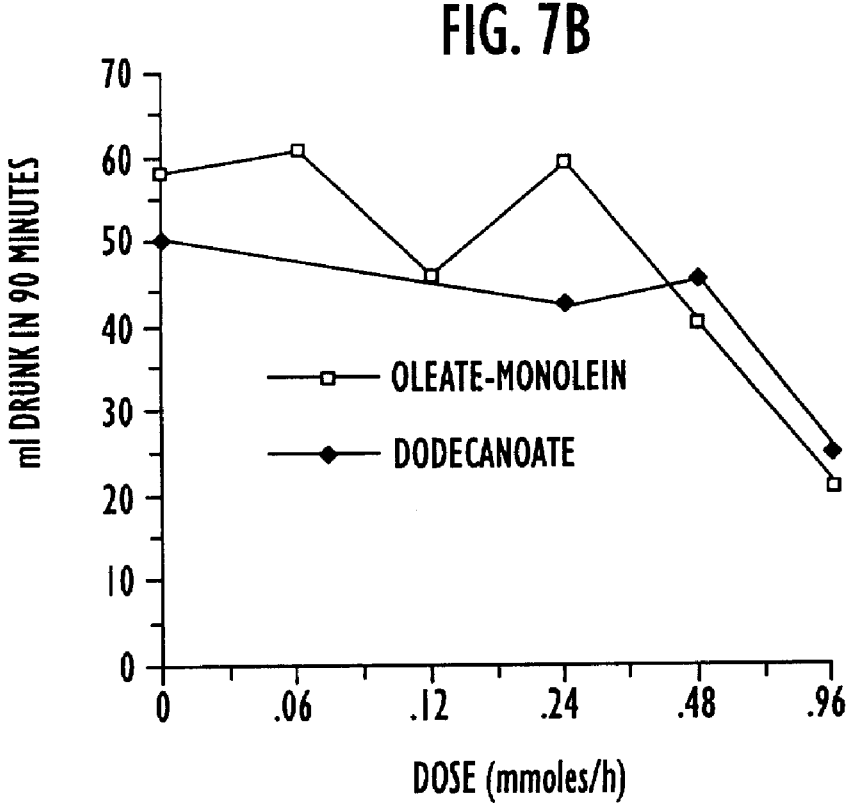
FIG. 7b is a fourth graphic representation of the results of Study 2B described below.

When dodecanoate was infused into duodenum or midgut in doses varied by varying its concentration, it was about as potent on a molar basis as the oleate had been at inhibiting sham feeding (FIGS. 7a and 7b).

As with amino acids (Study 2A), these results with fatty acids indicate (1) that the satiety responses were related to the load of fatty acid infused, independent of its concentration over the dose range studied and (2) that not all fatty acid congeners are active. The spectrum of activity (C12 & C18 >>> C10 or C8) is similar to that previously described for stimulation of pancreatic secretion (dog) or by luminal fatty acids.

Figure 8:
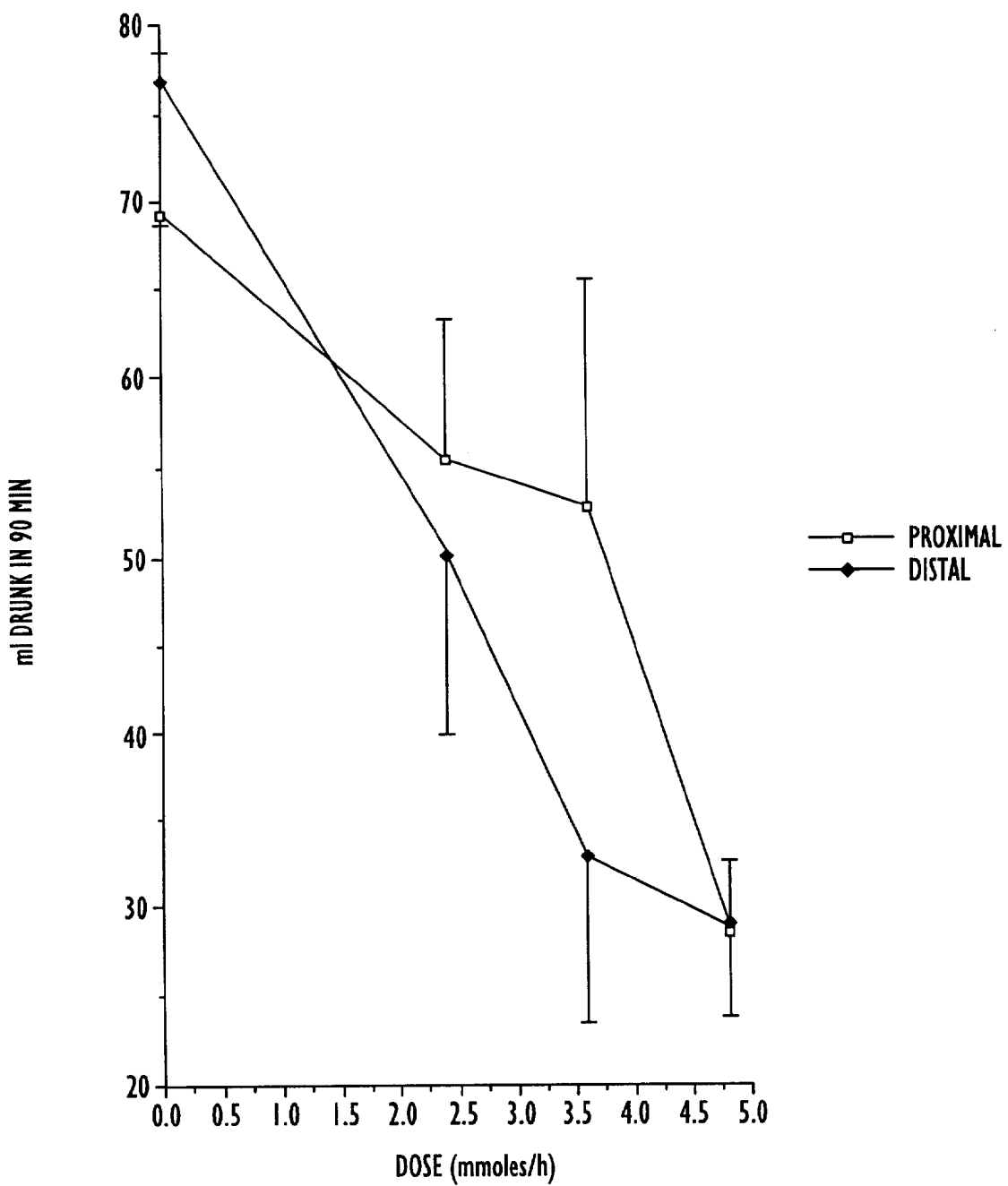
FIG. 8 is a graphic representation of the results of Study 2C described below.

Study 2C (Sugars):

The inventor has tested maltose, which is a dimer of glucose commonly released during hydrolysis of starch. Infusion of varied concentrations of maltose at 12 ml/h produced a dose-related ($p<0.01$) inhibition of sham feeding (FIG. 8), about equally when infused into either duodenum or midgut. The inventor also tested xylose and found that infusing 0.4M D-xylose (a naturally occurring pentose) into midgut at 12 ml/h (9.6 mmoles/h) did not reduce the amount nutrient drunk during sham feeding from that drunk during paired control perfusions with saline.

Figure 9:
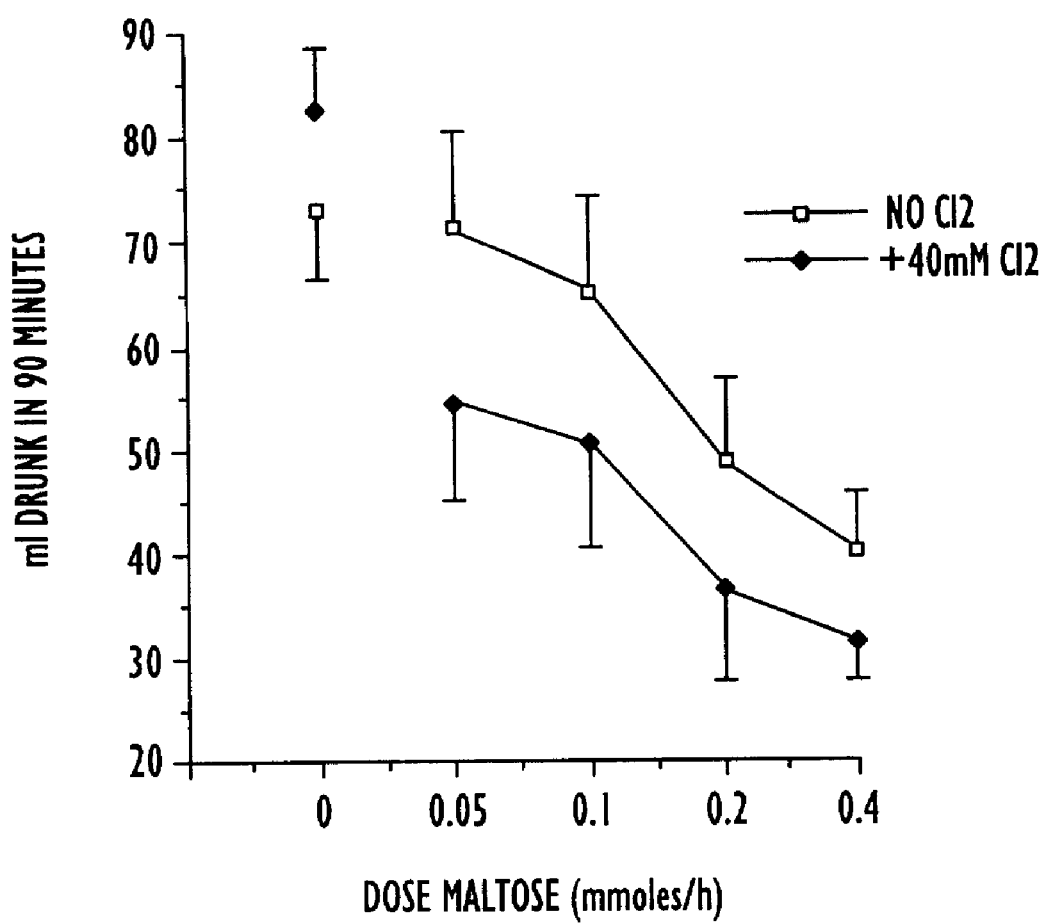
FIG. 9 is a graphic representation of the results of Study 2D described below.
Figure 10:
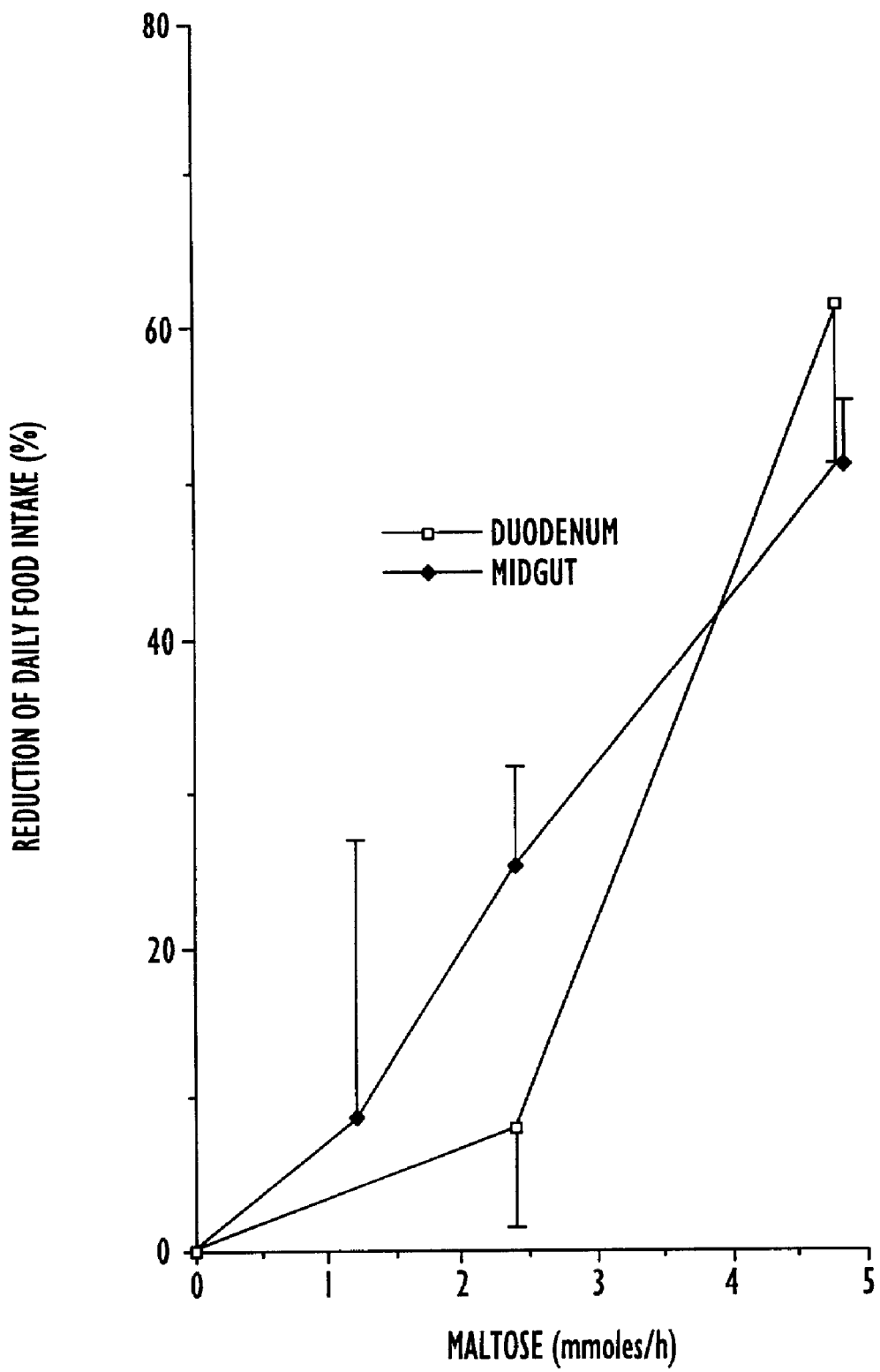
FIG. 10 is a graphic representation of the results of Study 3A described below.
Figure 11:
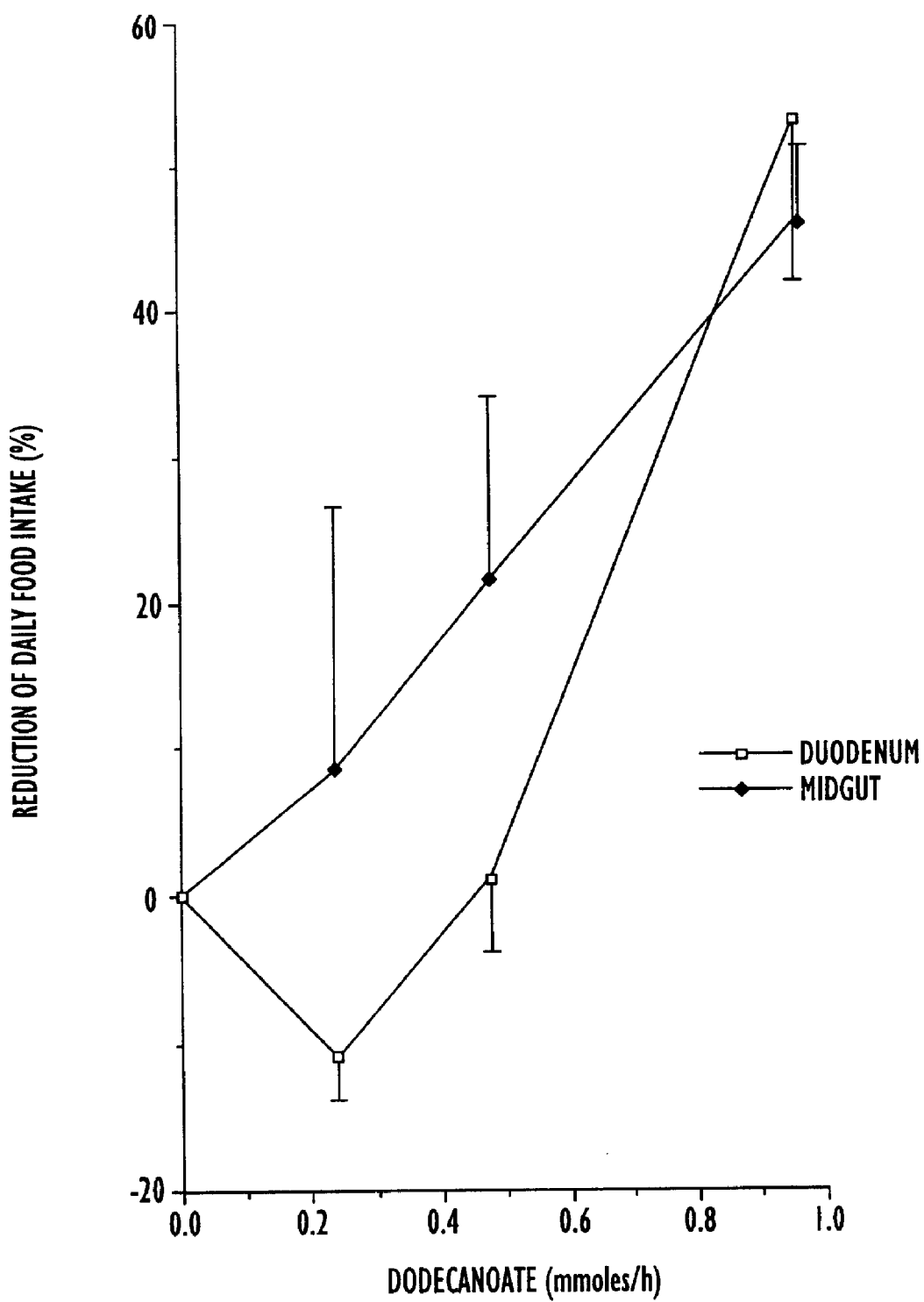
FIG. 11 is a second graphic representation of the results of Study 3A described below.

Study 2D (Interactions):

The sham feeding model also allows an exploration for interactions between two or more nutrients which individually inhibit sham feeding. To date, the inventor has studied only once such interaction (FIG. 9). The dose-response to varied concentrations of maltose infused at midgut was significantly increased when 40 mM dodecanoate (C12) was simultaneously infused at midgut, when compared to simultaneous control infusions of sodium bicarbonate+0 saline (pH 8.1 with same buffer strength as the dodecanoate).

Summary of Study 2:

These studies lead to the following conclusions: (1) With all three classes of common nutrients (amino acids, fatty acids, carbohydrates), only some congeners are active at inducing satiety. (2) With all three classes of nutrients, satiety responses in sham-fed rats could be generated during infusions at midgut which were of about equal magnitude with those generated on infusion into duodenum. These observations indicate potent sensors in ileum to all three classes of nutrients. (3) With both amino and fatty acids, satiety responses were dependent on the load of nutrient infused independent of its concentration over the range studied. In other systems of nutrient-driven, intestinal sensory feedback (stimulation of pancreatic secretion; inhibition of gastric emptying), load-dependence has been clearly shown to be the result of length of intestinal contact with the infused nutrient which increases directly with load; that is, the magnitude of the signal varies with the summation of responses of sensors along the length of contact. Such length-dependence predicted here from these studies with sham fed rats is currently being confirmed in Study 3B in naturally feeding rats that have undergone intestinal resections.

STUDY 3

A second rat model has been developed to permit the study of the effects of intestinally perfused nutrients on natural feeding. As with the sham-fed rats, infusion catheters are chronically implanted into duodenum and midgut, but this natural feeding model does not have a gastric fistula. Furthermore, the proximal ends of the infusion catheters exit from the subcutaneous tunnel at the back of the neck enveloped in a hard plastic, flanged overtube. The overtube is held in place by a sheet of dacron mesh sewn beneath the skin, over the flange, and bilaterally onto the neck muscles. The arrangement allows connection of the perfusion catheters to tubing from a syringe pump that run within a swiveled, wound wire sheath. Thus, the rats can be perfused at duodenum and/or midgut while freely roaming their cages; yet they cannot dislodge, bite, or break off the perfusing tubes. The rats are trained to eat from 1000–1300 h their entire day's ration (about 15 g) of powdered rat chow from dishes placed in their cages. By weighing the amount of food left at the end of the 3 h feed and subtracting this from the initial amount offered, the inventor has been able to measure the effect of various perfused nutrients on inhibiting food intake. Although the 1000–1300 h is enforced throughout the week, inhibition of food intake is studied only two days a week to allow the rats ample time to adjust their food intake between tests, respectively, upward or downward in compensation for net calories decreased or increased during perfusions on test days. Indeed, over long periods of time (one rat has been studied for 230d), the animals slowly gain weight and maintain a highly consistent average level of intake.

This freely feeding model has several advantages over the sham-fed model. First, control intakes (days of non-perfusion or of saline perfusion) are much more constant than control intakes in the sham-fed model. For example, daily intakes of rat chow over several months varied narrowly (the coefficient of variation for daily intake has average 0.16 among 9 rats). Second, the satiety response can be measured when food actually fills the stomach and intestines. This more natural situation than sham feeding allows for interactions between gastric distension and intestinal feedback not present in the sham-fed rat. Third, the net effectiveness of infused nutrients can be measured. Thus, the ratio of kcal in food not eaten (difference from control intakes) to the number of kcal infused is a daily measure of the efficiency of the infusate at inhibiting intake. Fourth, the animals feed each day during the tests (whereas sham-fed rats are fed for several hours each day after they are removed from restraint and the sham feed has been terminated). If infusions are performed daily (instead of twice weekly) cumulative caloric deficits and weight losses can be recorded as additional measures of the efficiency of the infused nutrient at inducing satiety and/or weight loss over time.

Figure 12:
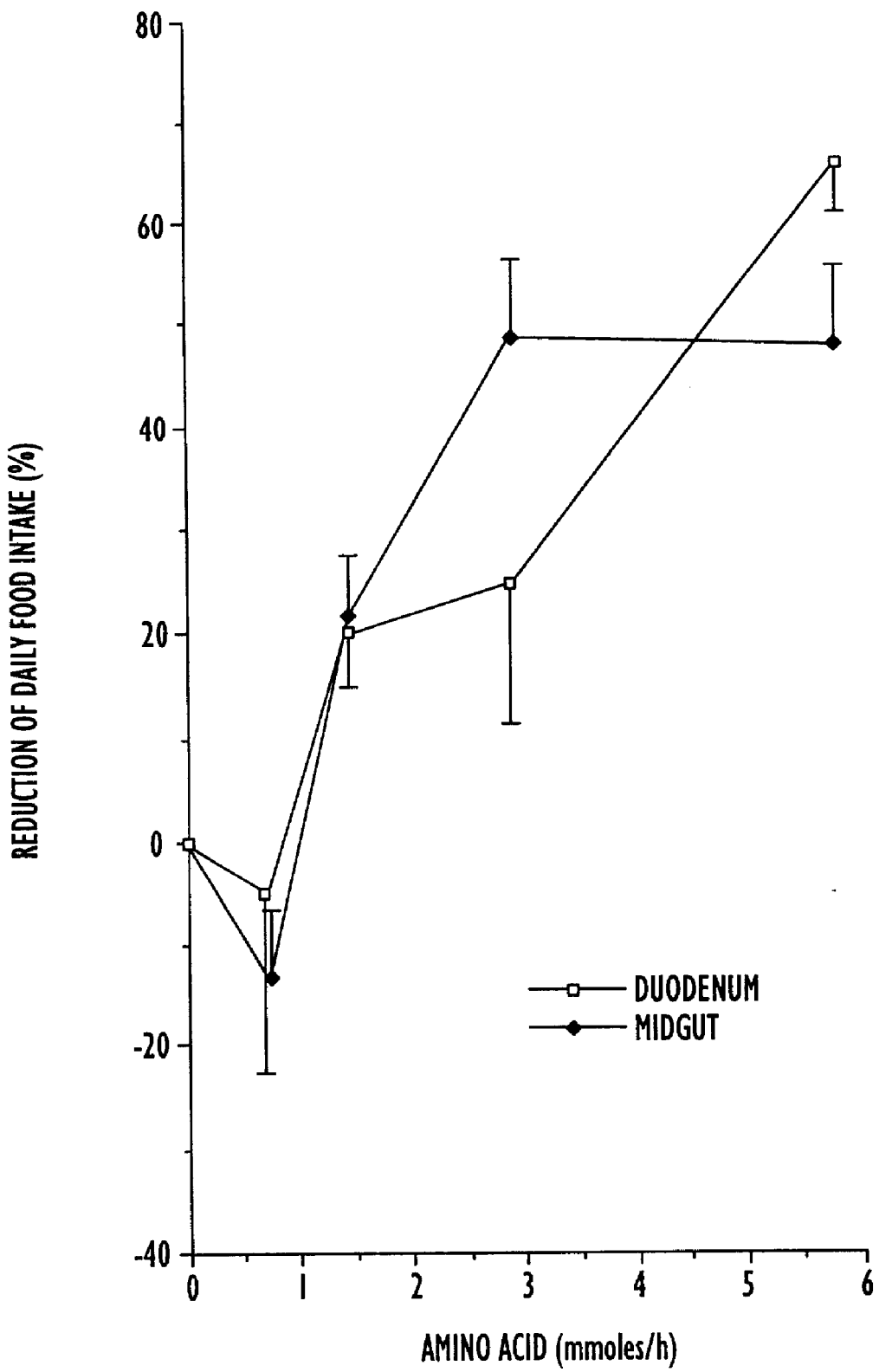
FIG. 12 is a third graphic representation of the results of Study 3A described below.
Figure 13:
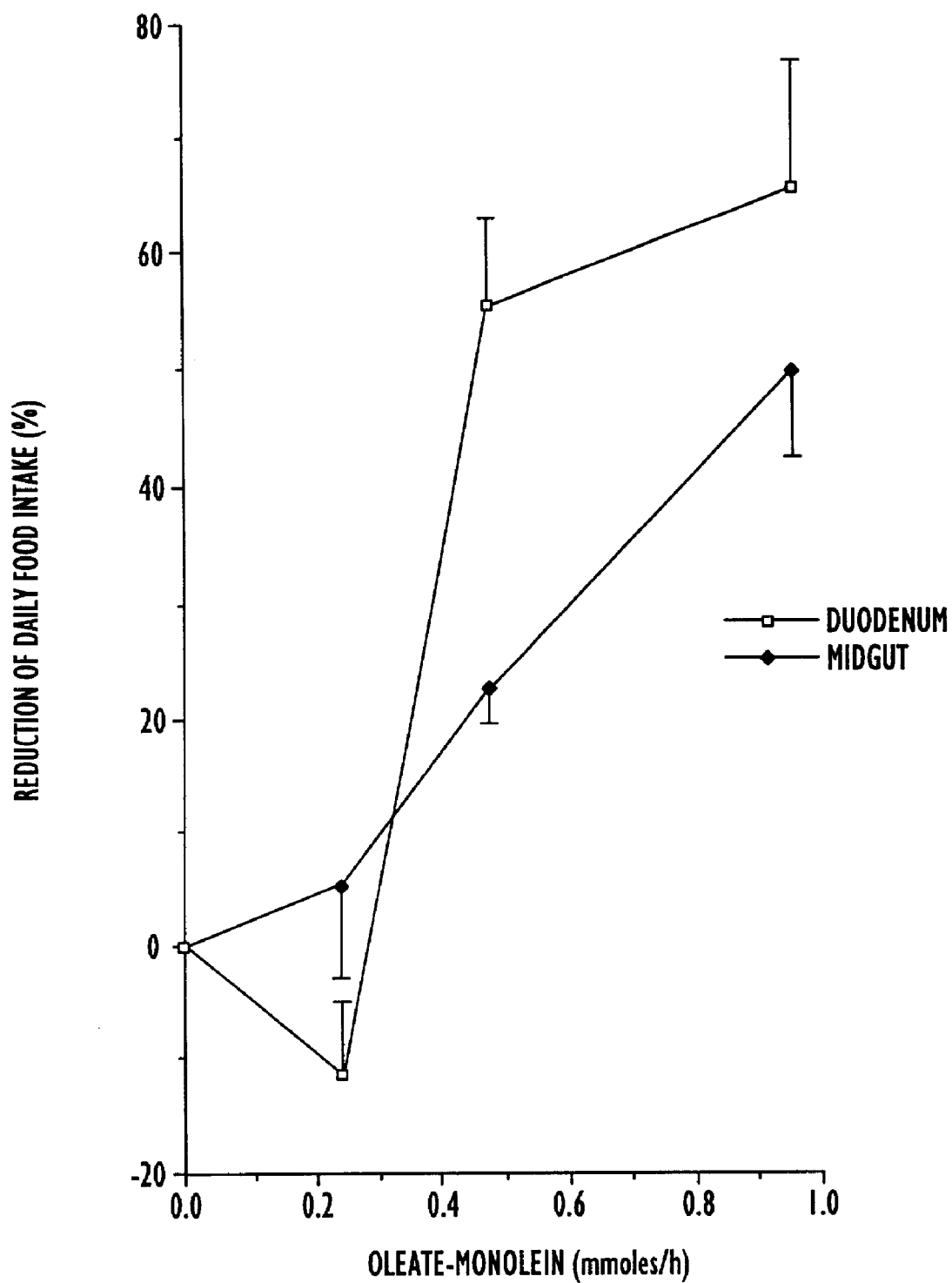
FIG. 13 is a fourth graphic representation of the results of Study 3A described below.
Figure 14A:
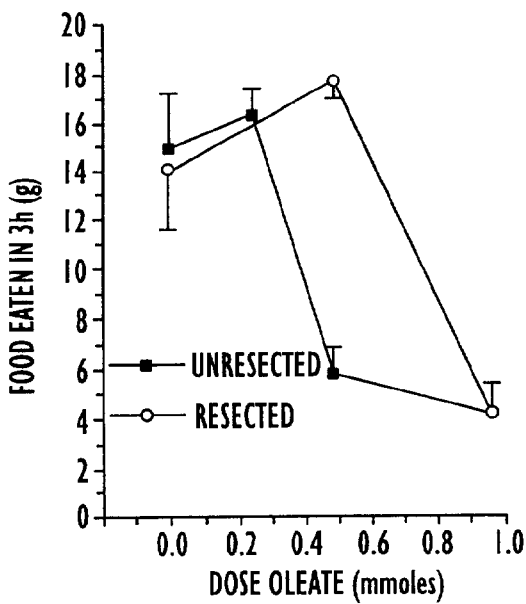
FIG. 14a is a graphic representation of the results of Study 3B described below.
Figure 14B:
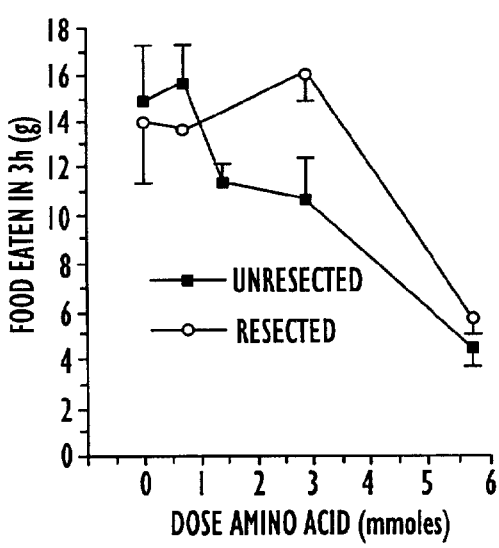
FIG. 14b is a second graphic representation of the results of Study 3B described below.
Figure 14C:
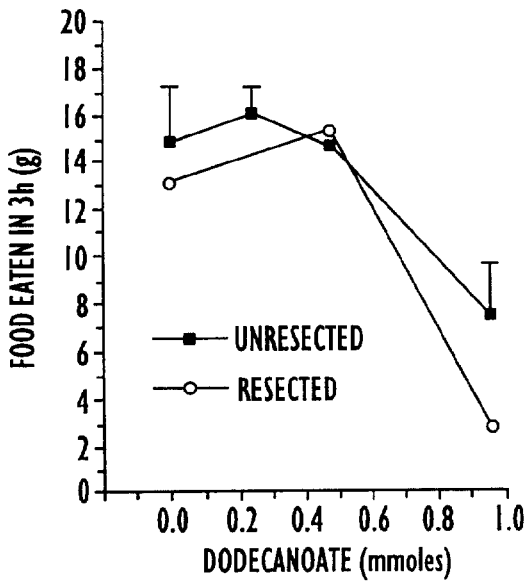
FIG. 14c is a third graphic representation of the results of Study 3B described below.
Figure 14D:
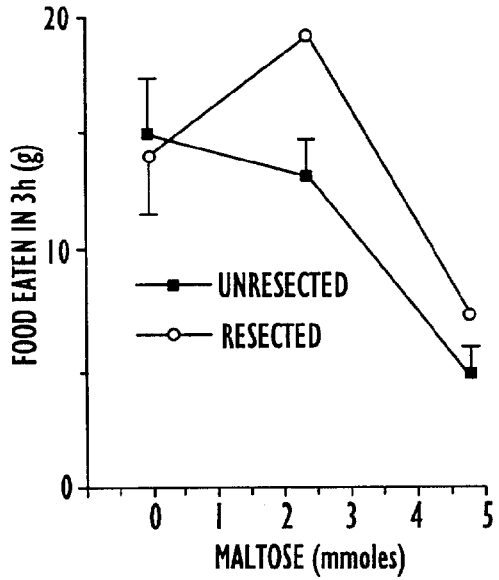
FIG. 14*d* is a fourth graphic representation of the results of Study 3B described below.

Study 3A:

In this study (as in Study 2) varied doses of maltose (0.4M), sodium dodecanoate (80 mM), phenylalanine (180 mM)+ tryptophan (60 mM) or oleate-monolein (20–8 mM) were infused at 3–24 ml/h into the duodenum or into midgut and effect of the various infusions on food intakes were measured (FIGS. 10–13). In most rats, each dose was tested more than once and the multiple responses in an animal were averaged to give one value per rat in calculations of means and standard error bars. With both maltose and dodecanoate (FIGS. 10 & 11), food intakes were suppressed more by the two lower doses when they were infused into midgut (i.e., were confined to ileum) than when the same doses were infused into duodenum; but the highest doses gave about the same amount of inhibition of intake when infused at either site. Although the response patterns with phenylalanine+ tryptophan were less clear, it was nonetheless evident that the 2.88 mmole/h dose produced a higher inhibition when infused at midgut compared to duodenum (FIG. 12). Also, a clear maximum inhibition (50% reduction of intake) was achieved when 2.88 or 5.75 mmoles/h of amino acid mixture was infused at midgut. When taken together, these three figures suggest that satiety feedback from lower loads of nutrients into ileum is about twice as effective as feedback from similar infusions into duodenum. The clearly lower maximum on midgut perfusion than on duodenal perfusion is consistent with (1) summation of responses between jejunum and ileum during high rates of duodenal perfusion, where amino acids spill into ileum; and (2) no effects of amino acids in colon into which they similarly spilled during perfusions into midgut. However, with oleate-monolein (FIG. 13), the opposite seems to be true; that is, infusions with this perfusate into duodenum were more potent than infusions into midgut.

Study 3B:

To limit access of duodenal perfusates to ileum, the freely feeding, perfused rat model was modified, so that the distal 50% of small intestine was resected to remove all ileal feedback. The duodenum of the rat was perfused with the same doses of nutrients as in Study 3A, and the effect of these duodenal perfusions on reducing food intake in the resected rat were compared with the effects of duodenal perfusions in unresected rats (from Study 3A). The ileal resection did not alter the satiety responses to duodenal maltose or dodecanoate. However, the ileal resection completely eliminated the satiety responses to all doses but the highest of duodenal phenylalanine+ tryptophan or of oleate-monolein (FIGS. 14a–d).

In FIG. 14, the error bars indicate the standard errors among unresected rats and the standard errors from multiple tests within the resected rat studied here. The magnitudes of these variances indicate real differences, as described above, between responses in the resected rat compared to those from the unresected rats.

From previously published canine studies of the inventor, it is known that oleate-monolein is very slowly absorbed from small intestine, at about $\frac{1}{10}$th–$\frac{1}{20}$th the maximal rate of intestinal absorption of glucose. These studies also indicated that sodium dodecanoate soap is absorbed 3 times more rapidly than oleate-monolein. In the presence of large quantities of amino acids, phenylalanine is also slowly absorbed, at a rate about 1.5 times that of oleate-monolein. Thus, the rates of absorption of these four perfusates were maltose>>dodecanoate>>phenylalanine-tryptophan>>>oleate-monolein. That the last was very poorly absorbed is further supported by the observation that oily diarrhea was almost always observed after the 0.96 mmole/h dose of oleate-monolein into either duodenum or midgut, whereas similar doses of dodecanoate infrequently produced diarrhea. Thus, ileal resection did not alter satiety responses from duodenal infusions of the more rapidly absorbed maltose or dodecanoate, but eliminated entirely responses to all but the highest doses of slowly absorbed phenylalanine+tryptophan and oleate-monolein. This observation indicates that the majority of the satiety responses to duodenal infusions of lower doses of the last two perfusates resulted from spillover of unabsorbed amino acid or oleate into ileum. The higher response of duodenal vs midgut infusions at the highest dose of amino acid or oleate (FIGS. 12 & 13) resulted from summation of response from jejunum alone to this very high dose (FIG. 14) plus ileal responses to the nutrient escaping absorption and spilling over into ileum. By contrast, both maltose and dodecanoate were already mostly absorbed in jejunum, so much less spilled over into ileum; and therefore ileal resection did not alter the satiety responses to these two perfusates. While each was nearly completely absorbed and confined to jejunum in the duodenally perfused, intact rats, each was capable of signalling satiety from the shorter length of contact of higher doses to jejunum alone (as confirmed in the resected rat); but responses to the lower doses of each in ileum were more effective than in jejunum.

This study therefore strengthens the ideas that (1) ileal feedback is more efficacious than jejunal feedback on satiety and (2) that; the magnitude of the satiety response results from a summation of feedback over the length of intestinal contact with the infused nutrient.

Study 3C:

The idea of summation of responses along length of contact is supported further by a study in which suppressions of intake were compared when dodecanoate was infused simultaneously into both duodenum and midgut and compared with suppression during infusions of similar amounts infused individually at either duodenum or at midgut (Table 3). The most marked suppression was achieved when 0.48 mmoles/h were perfused simultaneously into duodenum and midgut and was greater than when the same total amounts were perfused individually into either duodenum or midgut (but not both). It is likely that the greater responses during simultaneous perfusions at two sites resulted from a higher concentration along a longer length of bowel than during perfusions at either site alone. Thus, during duodenal perfusion alone, most of the 0.96 mmoles/h were probably absorbed before reaching ileum, so that any residual spilling over into ileum (the more effective site) was small in amount or concentration; while perfusion into midgut alone resulted in feedback from ileum (from which efficacy is twice as great as in jejunum), but no response from any excess spilling over into colon. By contrast, dividing total infusions of 0.96 or 0.80 mmoles/h into duodenum and ileum simultaneously, ensured that both sites (including the more effective ileal site) were exposed to high amounts (concentrations) of dodecanoate.

Study 3D:

The efficiency of satiety response from any dose of an individual nutrient in either jejunum (when infused into duodenum) or ileum (when infused at midgut) can be measured as: kcal of food intake reduced/kcal of nutrient infused to induce the reduction of intake. For simplicity, this ratio will be termed the "reduction ratio". This ratio has two practical uses: (1) it gives an indication as to which nutrient may be more efficient as a therapeutic satiety agent when delivered in a dosage form to the desired region of gut; and (2) it provides a further measure of differing efficacies of sensory feedback from intestinal regions undergoing perfusion with a satiating nutrient. Reduction ratios were measured during studies 3A & 3B.

Figure 15:
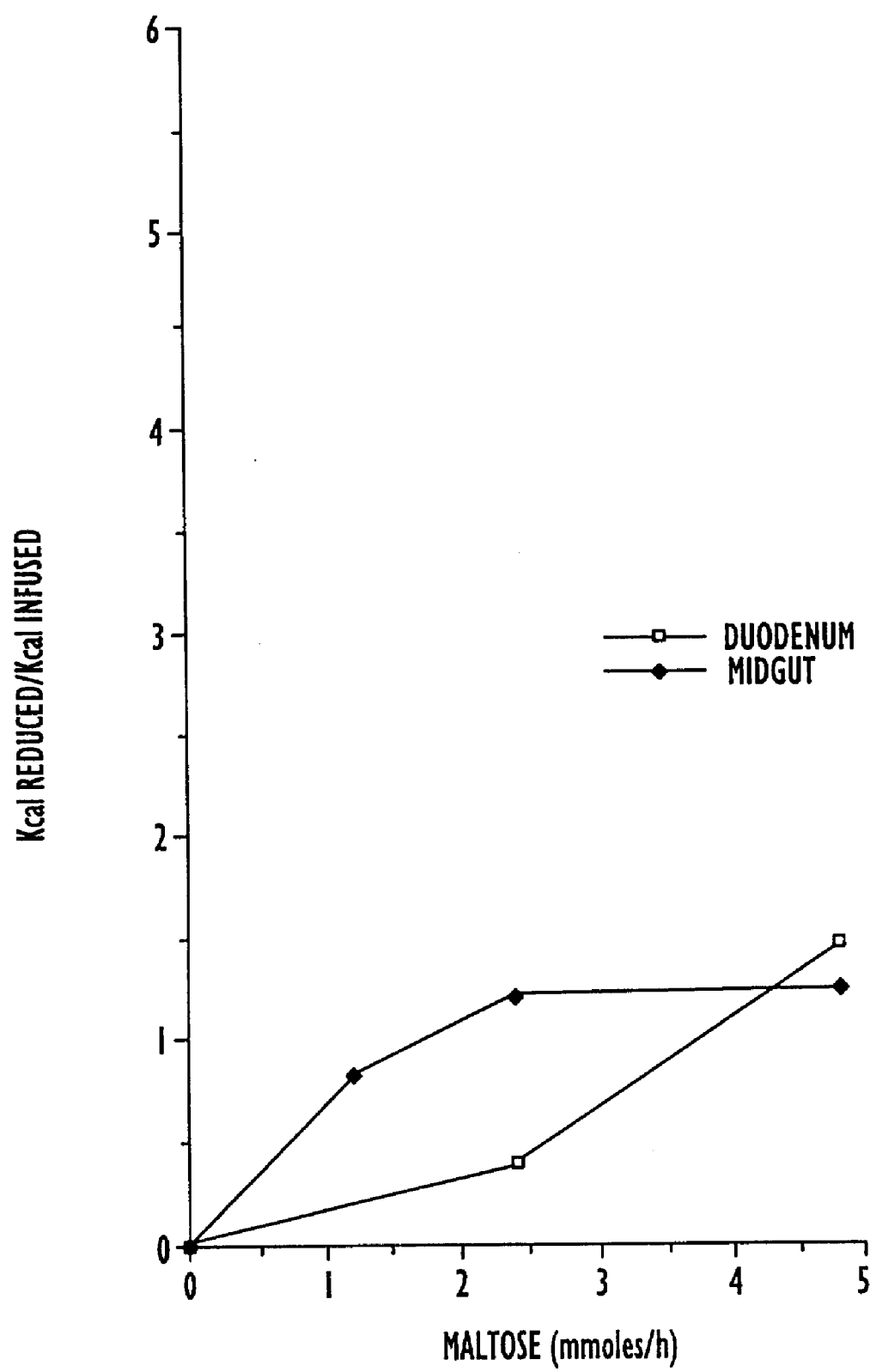
FIG. 15 is a graphic representation of the results of Study 3D described below.
Figure 16:
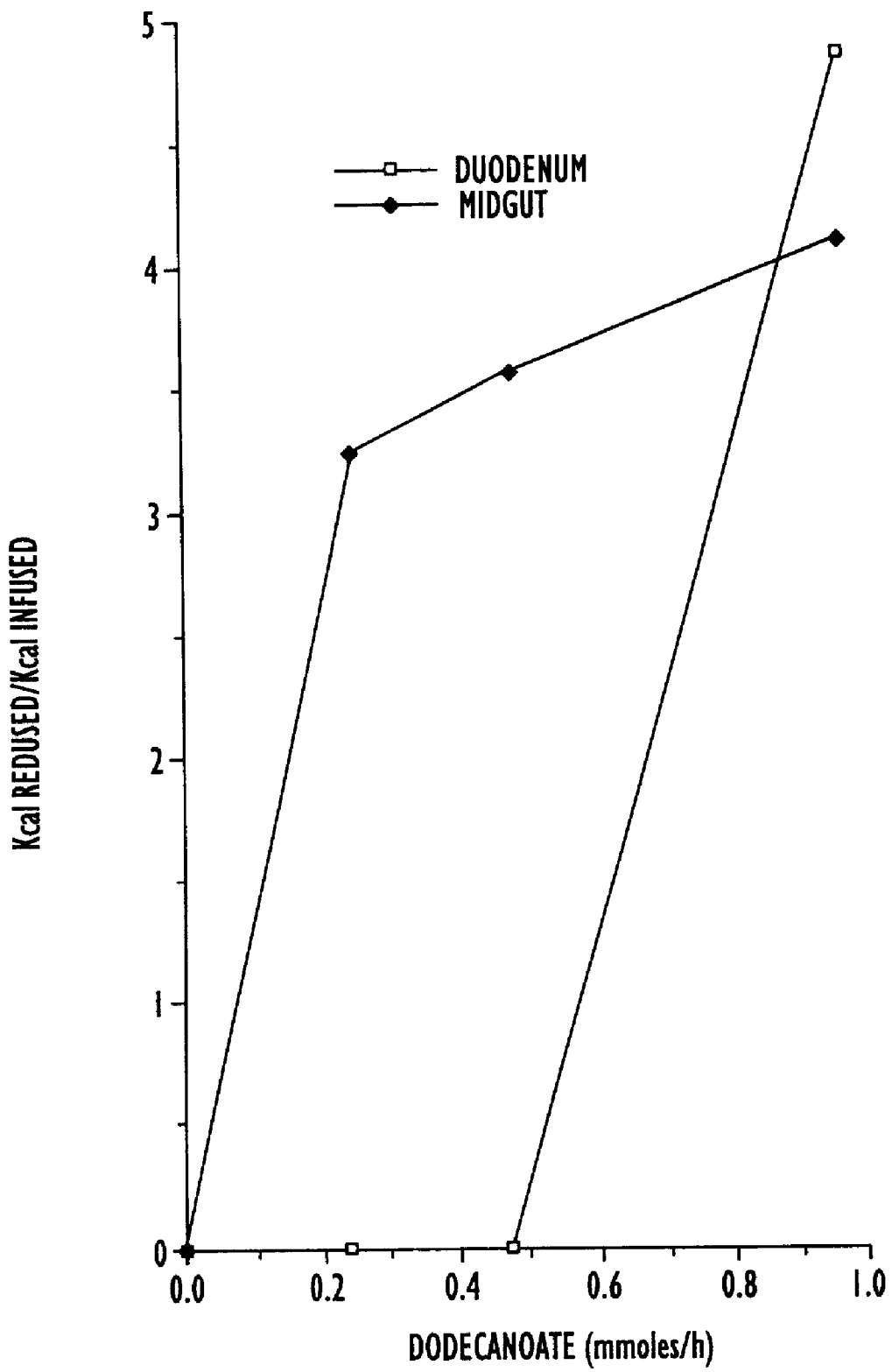
FIG. 16 is a second graphic representation of the results of Study 3D described below.
Figure 17:
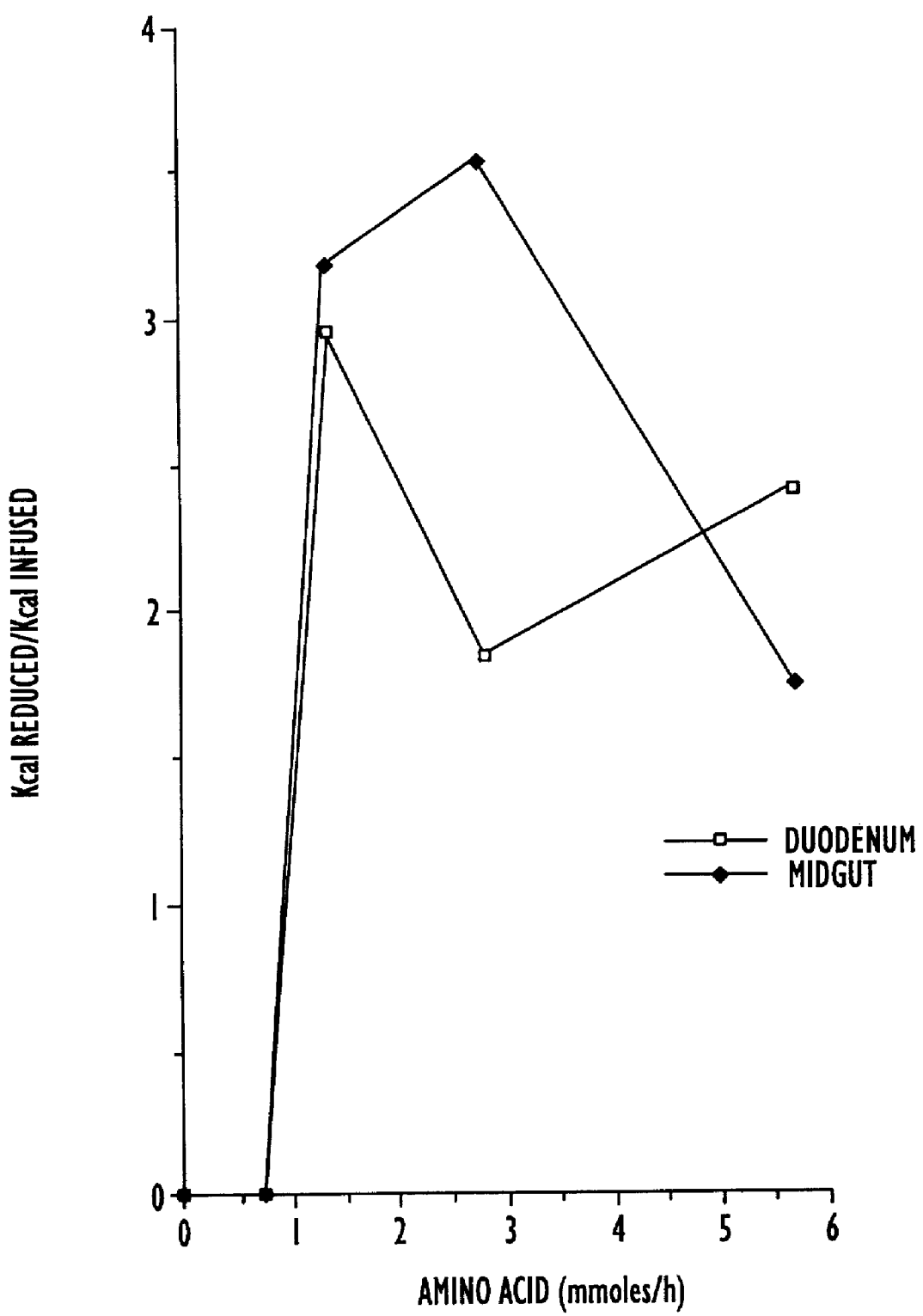
FIG. 17 is a third graphic representation of the results of Study 3D described below.

Reduction ratios with maltose ranged from 0.3 to 1.2 (FIG. 15). It was virtually constant at about 1.00 when all 3 doses of maltose were infused into midgut, but varied from 0.3 to 1.2 when maltose was infused into duodenum at 3.8 and 9.6 mmole/h doses. With dodecanoate (FIG. 16) the reduction ratio was also fairly constant, though considerably higher (3.25–3.75) when the soap was infused into midgut in doses ranging from 0.24 to 9.96 mmoles/h. When dodecanoate was infused into duodenum, the ratio fluctuated from zero with the lower two doses to 4.7 with the highest dose. With phenylalanine+tryptophan (FIG. 17) the ratio was fairly constant (2–3) when the amino acids were perfused at either site. At the lower doses of amino acids the ratios were again higher in ileum than jejunum.

Thus, with all three of these nutrients reduction ratios were consistently higher during perfusions into ileum than during duodenal perfusions. Moreover, they were fairly constant in ileum over the ranges of doses. These two observations indicate that targeting the pharmaceutical delivery of nutrients to ileum will produce (1) a higher and (2) more consistent reduction ratio than delivery of nutrients to jejunum.

Figure 18:
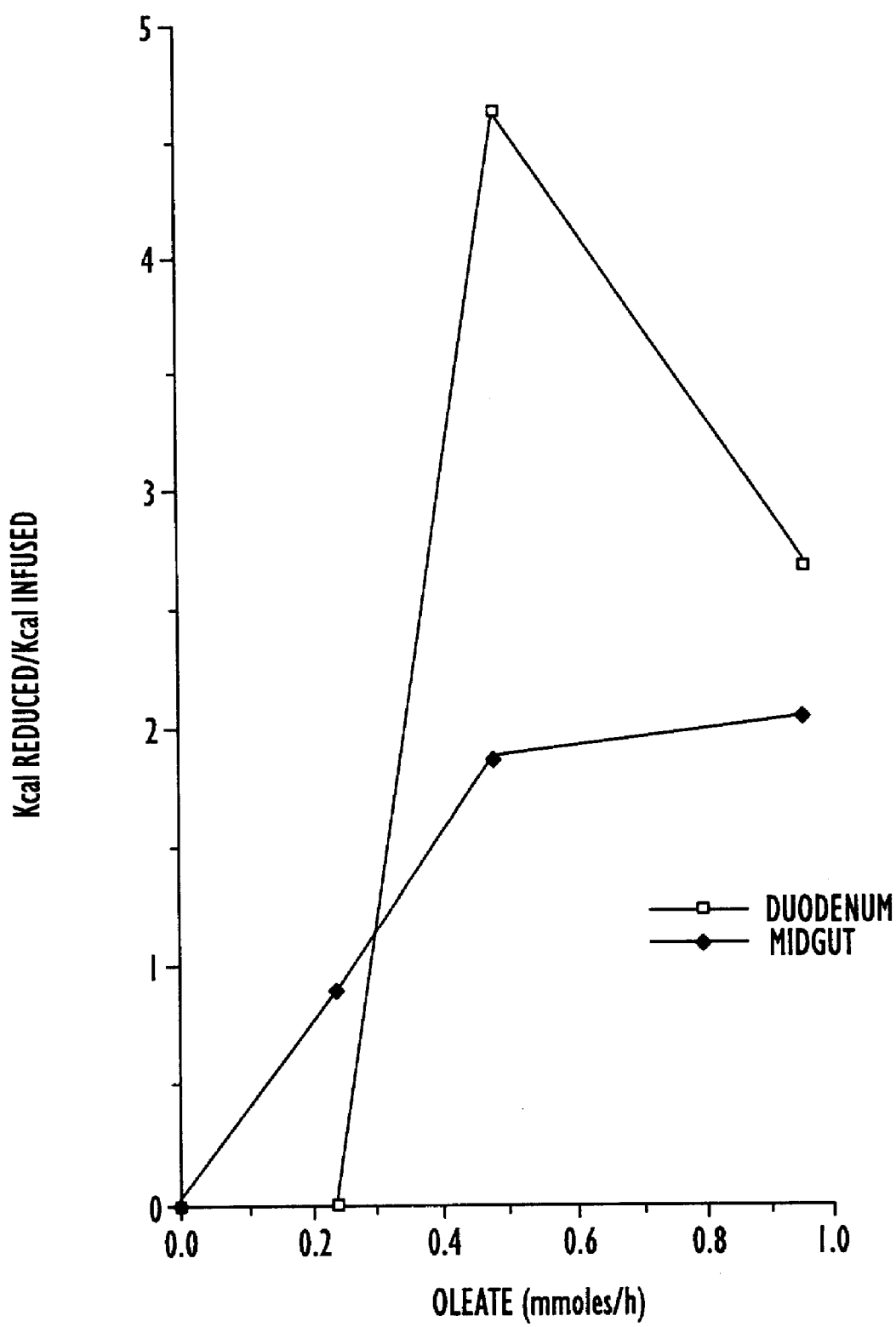
FIG. 18 is a fourth graphic representation of the results of Study 3D described below.

With oleate-monolein (FIG. 18), however, reduction ratio was higher on duodenal perfusion of 9.48 mmoles/h than on duodenal perfusion at 9.96 mmoles/h and higher than the fairly uniform ratios (1–1.8) across the range of doses infused into midgut. Undoubtedly, the wide fluctuations of the reduction ratios during duodenal perfusion reflected the very slow rates of intestinal absorption of the oleate-monolein (see Study 3B). Thus, the very steep rise of the ratio from 0.0 to 48 when the duodenal dose was increased from 0.24 to 0.48 mmoles/h probably reflected spread of oleate over the entire small bowel to produce a maximally summated response; while further increase of the duodenal dose from 0.48 to 0.96 mmoles/h produced a fall in the reduction ratio because some of the oleate was now spilling over into colon (from which there is no feedback), as evidenced by the development of oily diarrhea in these animals.

Figure 19:
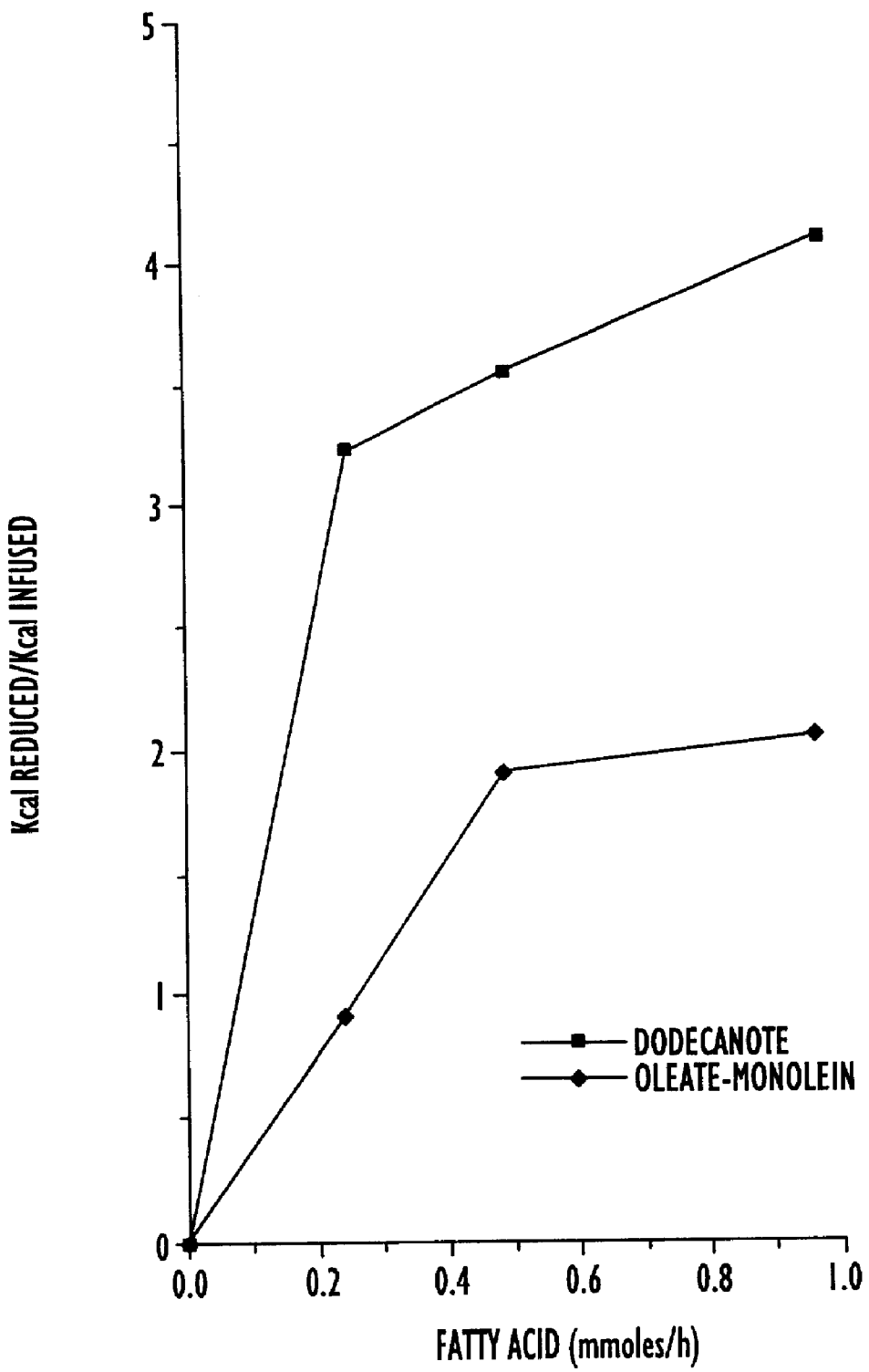
FIG. 19 is a fifth graphic representation of the results of Study 3D described below.

A further point to be made is that the reduction ratios can be maximized by proper selection from among active nutrients. For example, though perfused maltose induces satiety, its reduction ratio of about 1.0 would make it a less effective agent than perfused fatty or amino acids, which have reductions ratios greater than 3.0. Even among congeners within a class of nutrients, selection can enhance efficacy. Thus, dodecanoate (⅔rds the molecular weight of oleate but equipotent with oleate on a molar basis) gave an ileal reduction ratio that was 33% higher than ileal oleate (FIG. 19). Potentially synergistic interactions between nutrients of different classes (Study 2D) may also enhance effective reduction ratios. While there may be other pharmaceutical considerations for choosing a particular nutrient or combinations of nutrients (for example, chemical compatibility with dosage forms, ease of coating, or considerations of densities of the dosage form), even within these limitations selections can be made to maximize the reduction ratio in the final product.

It is also evident that the reduction ratio may be increased by achieving a more effective intestinal distribution of the satiating nutrient. Thus, with dodecanoate, it was increased from 4.1 to 6.8 simply by redistributing the infusion so as to maximize its length of contact with small intestine (Table 3).

The final point is that the reduction ratios here were observed during intestinal perfusion into duodenum or into midgut. These infusions of nutrient in solutions is the only practical way to deliver nutrients to proximal vs. distal intestine in this animal model. Since there is active intestinal absorption of the nutrients from the infusions, the observed reduction ratios reflect the amount of nutrients that had to be infused to exceed absorption and to spread nutrient along a sufficient sensory length of small intestine to produce a high satiety response. For example, the tenfold higher effective molar dose-range of maltose compared to oleate-monolein or dodecanoate undoubtedly reflects its tenfold faster molar rate of intestinal absorption. So also, its low reduction ratio (of about 1.0) compared to dodecanoate (with reduction ratio of 3–4). However, in the full embodiment of this invention, nutrients will be delivered via a dosage form that will spread the release of nutrients along ileum. Since, under this embodiment, spread of active nutrient ingredients along ileum would no longer depend on introducing relatively large amounts of nutrient at the proximal end of the ileum to overwhelm ileal absorptive capacity, we expect that the reduction ratios actually achievable with full embodiment will be several fold higher than those observed here.

STUDY 4

Figure 20:
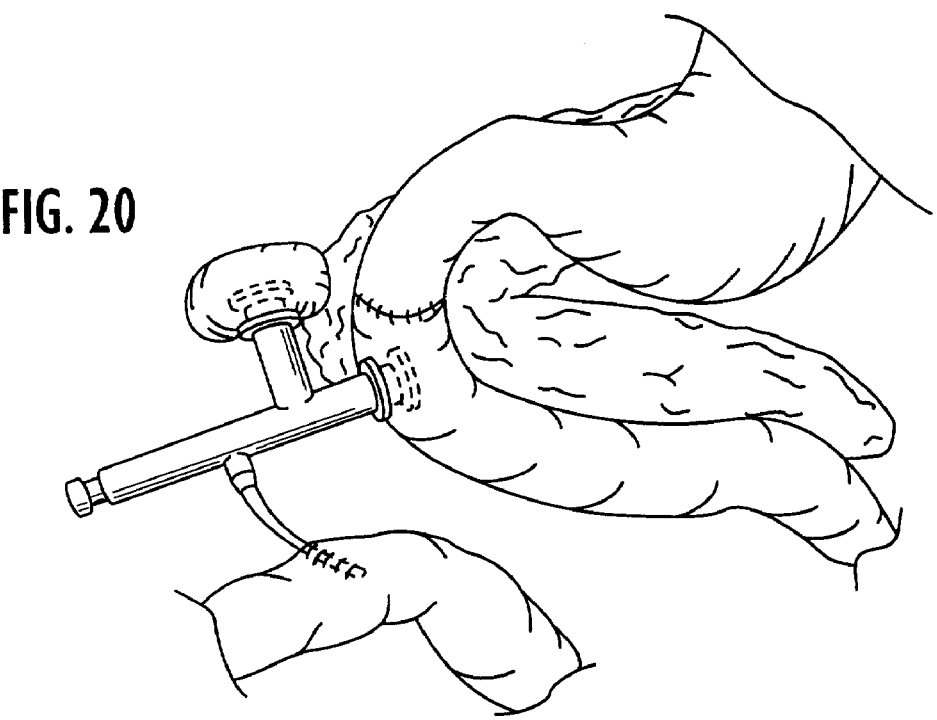
FIG. 20 is a representation of a chronic Herrera pancreatic fistula in a dog as modified for the purposes of Study 4 described below.

The studies on ileal satiety mechanisms were conducted in dogs equipped with chronic Herrera pancreatic fistulas, with a modified design. To create these fistulas, the minor pancreatic duct was ligated; and the portion of the duodenum into which the main pancreatic duct drains was removed from duodenal continuity by transection above and below the duct. This portion of duodenum was then fashioned into a closed, collecting pouch by over-sewing its ends. Duodenal continuity was re-established by suturing the cut ends of the duodenum back together. A stainless steel Herrera cannula which forms a sort of asymmetrical T, was then inserted so that the sidearm drained pancreatic juice from the collecting pouch while one end of the long arm entered the duodenum and the other end exited from the abdomen through a skin incision. When the cutaneous end was kept closed, all pancreatic juice entered the duodenal pouch, flowed thence through the sidearm of the Herrera cannula and into the long arm and from there into the duodenum, so that digestion remained normal. A standard Herrera cannula was used whenever an investigator wished to collect pancreatic juice or to divert pancreatic juice from the duodenum during repeated, acute experiments. This was done by inserting an obdurator, essentially a plug on a long stem that blocks the duodenal end of the long arm of the Herrera cannula while reversing flow of juice out the cutaneous end. The modification (FIG. 20) used in this study involved putting a second sidearm in the form of a nipple on the Herrera cannula. One end of a short piece of Tygon tubing was attached to the nipple, while the other end was tunneled through and secured in the bowel wall at the midpoint of small intestine. (To do this, the surgeon pulled the mobile small intestine toward the Herrera cannula, so that the distance the Tygon tube had to traverse was quite short).

Figure 21:
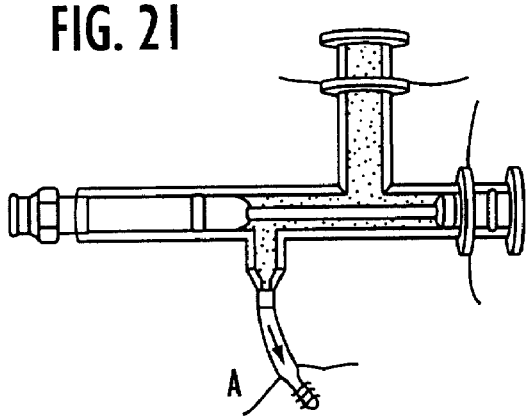
FIG. 21 is an enlarged view of FIG. 20, showing the modified Herrera cannula into which has been inserted an obdurator which directs the flow of pancreatic juice into the ileum.
Figure 22:
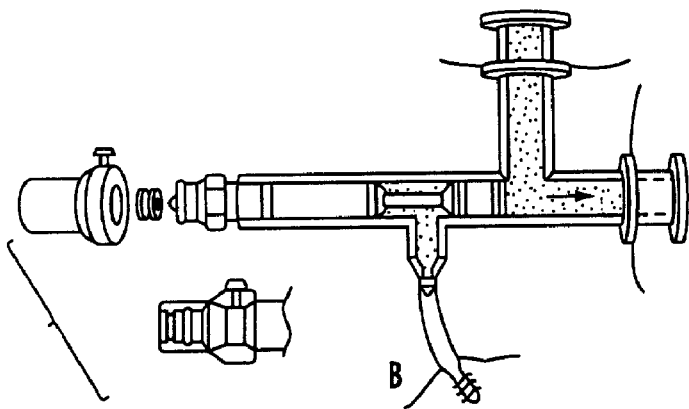
FIG. 22 is an enlarged view of FIG. 20, showing the modified Herrera cannula into which has been inserted an obdurator which directs the flow of pancreatic juice into the duodenum.

As illustrated in FIGS. 21 and 22, detailed drawings of the cannula design, two different obdurators, equipped with double O-rings to provide water tight seals, were used to direct the flow of pancreatic juice, either into the duodenum (FIG. 22), the normal situation, or into the distal half of small intestine (FIG. 21), an abnormal route. The routings could be changed in about 2 minutes by unscrewing the cover cap (FIG. 22), which is outside the abdominal wall, changing the obdurator, and replacing the cover cap. The obdurator in FIG. 22 was also designed so that water could be injected under pressure through the Tygon by-pass conduit to assure its patency through such periodic irrigations. This study was a double crossover design to minimize the effects of weight loss; that is, only eight day periods were used so that any weight loss would be limited to minor amounts. It was an objective of the study to determine how digestion in the proximal bowel (the normal pathway) vs. in the distal bowel, affected food intake. Since weight loss stimulates the brain to override normal satiety mechanisms, profound weight loss could mask real differences in satiety responses between proximal and distal digestive pathways. Thus, the protocol was designed so that after a base line period of normal digestion, the dogs would undergo four successive 8 day periods. The subject dogs were designated either group A dogs or group B dogs. In group A, pancreatic juice was diverted to distal intestine for the first 8 day; it was then returned to duodenum for the second 8 day; for the third 8 day period it was again diverted to distal bowel; and in the final fourth 8 day period, it was again returned to the duodenum. In group B, pancreatic juice entered the duodenum in the first 8 day period, and then in successive 8 day periods, the distal bowel, the duodenum and finally the distal bowel. Wherever the pancreatic juice was going, the dogs had the obdurators changed every 4 days so that (a) the by-pass conduit could be irrigated and (b) the manipulators would be multiplied so that the dogs could less easily understand how they were being manipulated (i.e., they were blinded to their treatments). Whatever the treatment, the dog was allowed to eat freely from a bucket which contained 4000 grams of a standard kibble dog food.

At the same time every morning for each of the 32 days of the study, the bucket was weighed to determine the amount of dog food consumed in the 24 hour period. Also, every second day, each dog was weighed. The dogs were housed in outdoor kennels, so there was no control of environmental temperature. However, studies were conducted throughout the year so that there was no seasonal bias. Eleven dogs were studied, six: dogs in group B and five dogs in group A.

Figure 23:
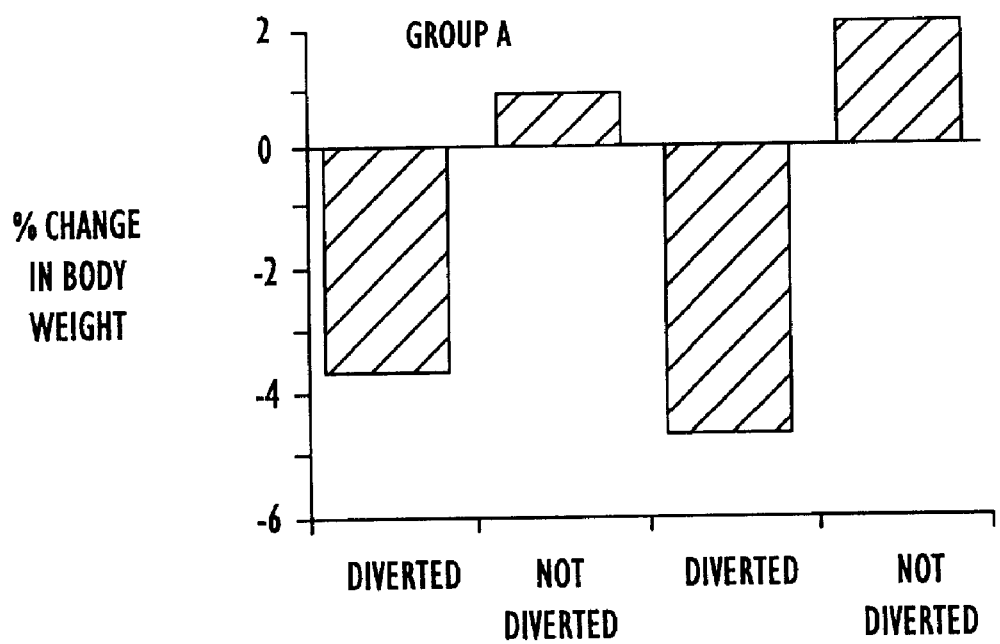
FIG. 23 is a graphic representation of the results of the Study 4 described below.
Figure 24:
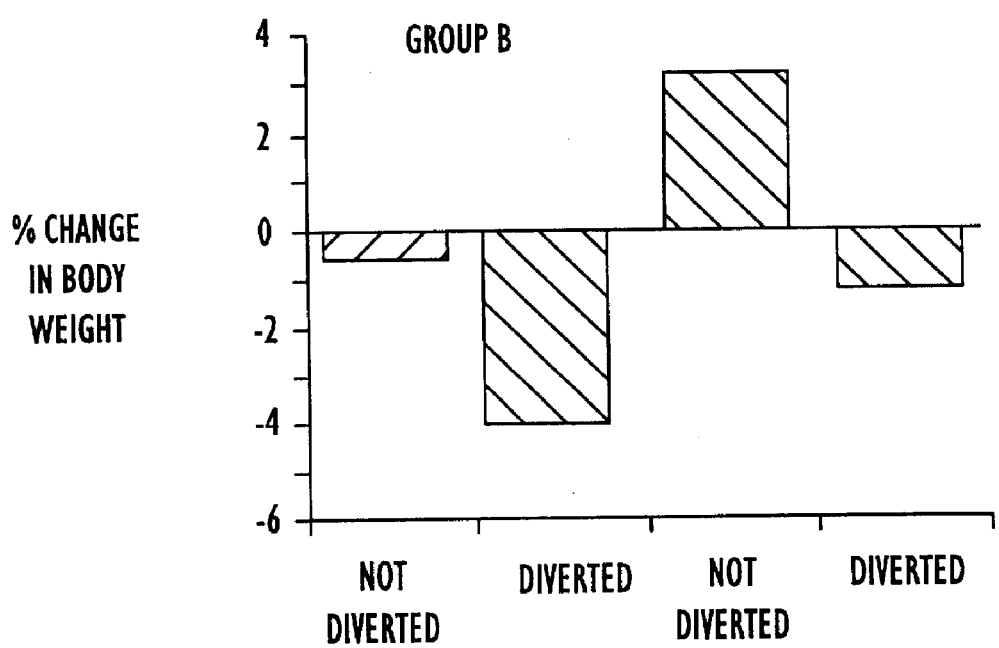
FIG. 24 is a second graphic representation of the results of the Study 4 described below.
Figure 25:
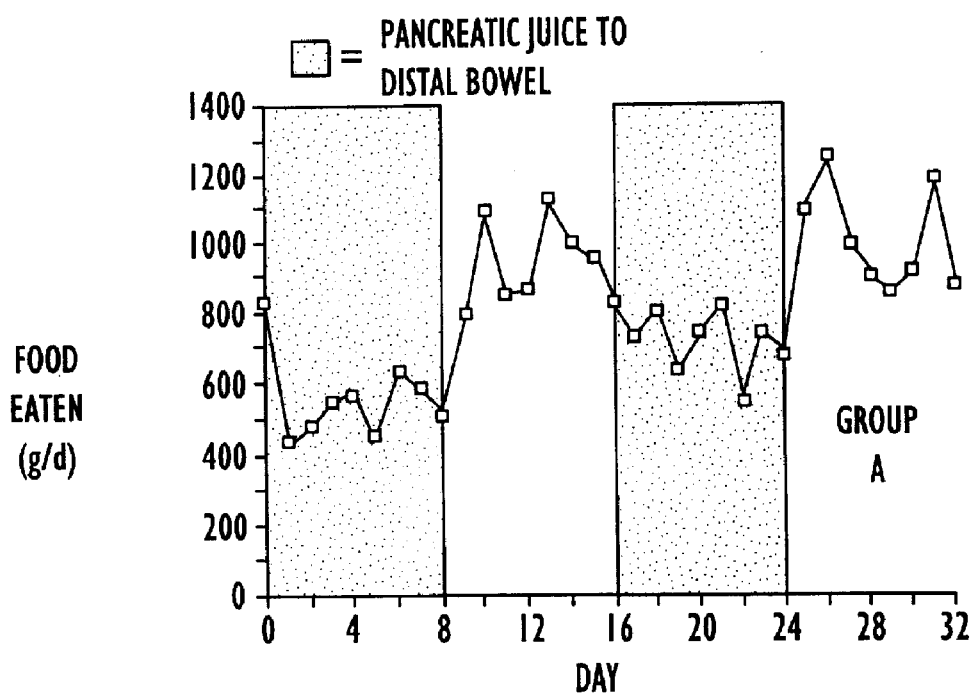
FIG. 25 is a third graphic representation of the results of the Study 4 described below.
Figure 26:
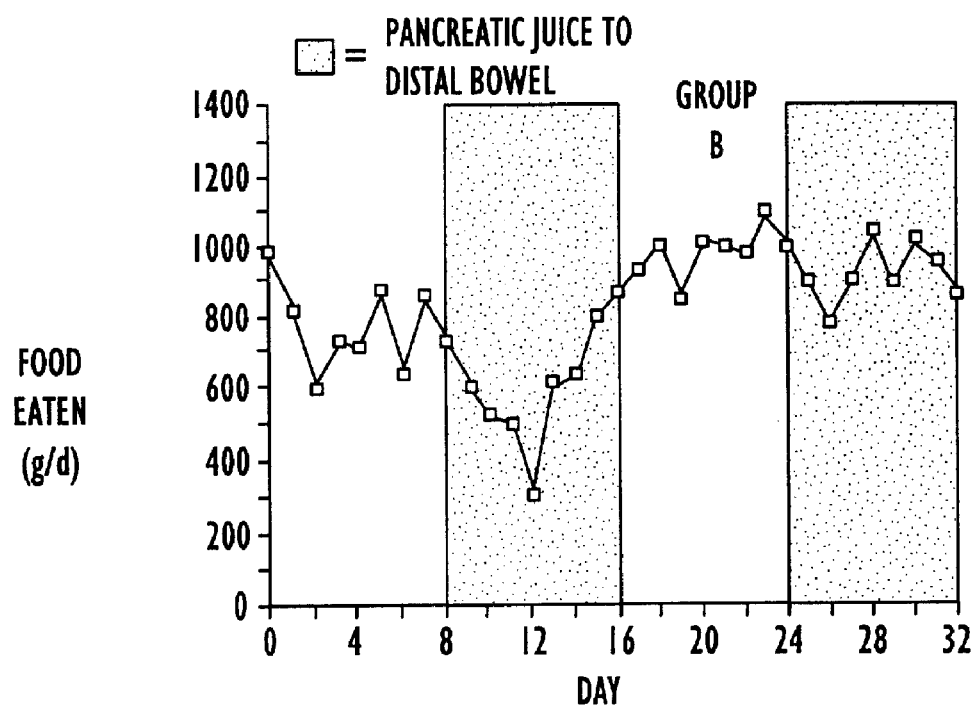
FIG. 26 is a fourth graphic representation of the results of the Study 4 described below.

In either group, diverting the pancreatic juice to the distal bowel consistently reduced food intake (FIGS. 25 & 26) and body weight (FIGS. 23 & 24). The magnitude of the reduction in food averaged (between the two periods of diversion within dogs) in individual dogs from −12% (only one dog showed no reduction) to 52%. The "gorgers" (those dogs that tended to wolf down their food quickly in one large daily feed) were less affected by pancreatic juice diversion than the "nibblers" (those dogs that ate small amounts frequently throughout the day). The one dog that did not respond was a pronounced "gorger." Food intake and percent weight change during the two periods of diversion were averaged in each animal and compared by paired T test with the corresponding average in the same animals from the two periods of normal, duodenal entry of pancreatic juice. Food intake was statistically significantly ($p<0.005$) lower and weight loss was statistically significantly ($p<0.0005$) greater in the 11 dogs during the periods of diversion of the pancreatic juice to the distal small intestine.

The patterns that emerged from the double crossover design strongly support the idea that distal routing suppressed appetite. Thus, as impressive as the diminished food intake during the periods of diversion, was the rebound hyperphagia when the juice was routed back to the duodenum in the next 8 day period.

STUDY 5

Tethered rats can be perfused daily while freely feeding, and the effects of daily perfusions on food consumption and body weight can be measured each day. The daily perfusions allow observation of cumulative caloric deficits and loss of body weight on responses to infusates. By contrast, tethered rats in Study 3 were perfused twice weekly on a schedule designed to minimize weight loss and thus eliminate the impact of weight loss on response to the infused satiety agent.

Figure 27A:
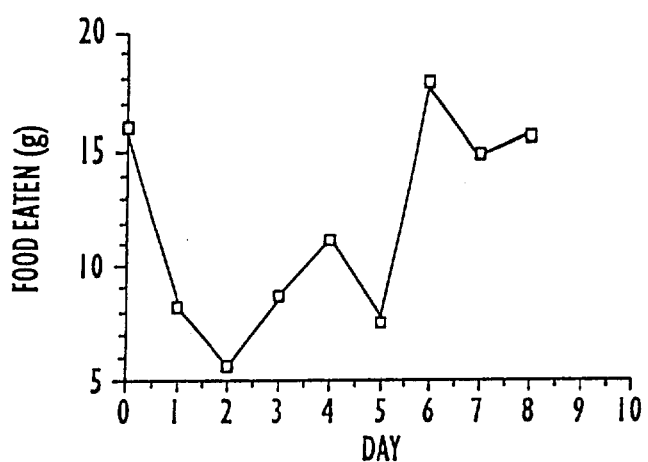
FIG. 27*a* is a graphic representation of the results of the Study 5 described below
Figure 27B:
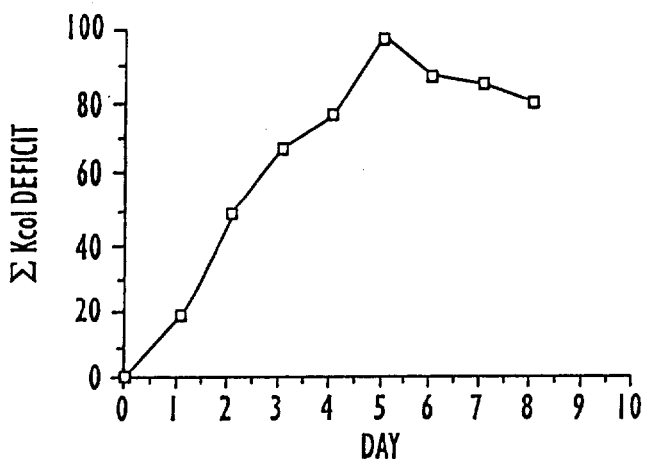
FIG. 27*b* is a second graphic representation of the results of the Study 5 described below.
Figure 27C:
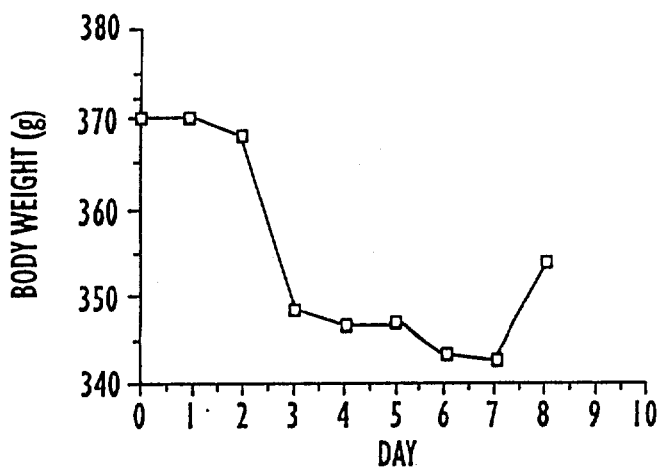
FIG. 27*c* is a third graphic representation of the results of the Study 5 described below.

A rat was studied for 8 days of perfusion (FIG. 27). This rat is being perfused with oleate-monolein during its 3 hour, daily feeding period. This infusate has consistently exhibited a reduction ratio of 4.5 when given on a twice weekly basis. When given on a daily basis, here, it initially reduced intake of food by about 50% (FIG. 27A). This reduction of food intake was associated with loss of 9% of pretest body weight (FIG. 27B) and a cumulating caloric deficit (FIG. 27C). The last was calculated from the rat's steady daily intake over weeks before the test: daily caloric deficit equals (average pretest daily caloric consumption+ calories infused as oleate) minus calories eaten during the oleate infusions. It can be seen that while the infused oleate initiated weight loss, some adaptation emerged by Day #6 so that the suppressant effect of the oleate was reduced. Quite clearly, the oleate inhibited food consumption and induced weight loss when infused into the small intestine in a spatial and temporal pattern that maximized its reduction ratio. On the other hand, the rat seemed to adapt with time to the oleate so that its intake returned toward normal.

However, switching the rat to the phenylalanine-tryptophan suppressing nutrient system resulted in a 60% suppression of calorie intake. This demonstrates that the adaptation is nutrient specific and may be overcome by concurrent or sequential use of varying suppressing nutrient systems.

STUDY 6

Determination of Optimal Nutrient(s). The object of this study is to find the most potent inhibitor at the most sensitive site. 100 rats with chronic cannulation of intestine are chronically fed over several successive days. A selected site along each rat's intestine is surgically linked to an 8 channel, small volume perfusion pump using standard techniques. Single or two-channel tethers are used to allow rat free movement and feeding during the study. The ileum or other selected segment of gut, is perfused with either NaCl as the control or with the nutrient to be tested, before and during daily feeding times. Food consumption during perfusion is measured. Dose-response data is generated, to show relative potencies of glucose, oleate, dodecanoate, phenylalanine, and various polypeptides infused in the ileum and in other parts of the intestine. This assay model may be used to determine whether combinations of nutrients are more potent than single nutrients; and/or whether multiple delivery sites are better than a single region of the bowel. Also, simultaneous infusion through two spaced infusion ports in terminal ileum might may be used to determine whether spaced release, as opposed to single point release, enhances potency. The advantages of this assay are that chronic feeding, testing of agent over several successive days, causes less perturbation than acute, sham-feeding, models; it also allows a determination as to whether the effect wears off with time.

STUDY 7

Confirmation in Man: The optimal nutrient or nutrient combination determined from example 6 is tested in normal volunteers independently of any dosage form, using chronic intestinal intubation with single or multilumen perfusion tubes properly sited along the bowel. Again, the amount of food consumption during perfusion of nutrient is measured against the amount of food consumption during perfusion of the control. Two 1 mm perfusion lumens are easily tolerated for several days by experienced or naive subjects. A four day test schedule per subject allows adequate comparison of 2 doses of nutrient against control infusions.

STUDY 8

Preliminary dosage formulation: Glucose in ileum is 4 times more potent at inhibiting gastric emptying of solid food than glucose in jejunum. Therefore, to test an ileal delivery system, doses of glucose are separately coated with a rapidly dissolving coating (one that comes off in the duodenum) and with a delayed release coating (one that comes off in the ileum). Thus, the ileal-releasing preparation should significantly inhibit gastric emptying more than the jejunal-releasing preparation. The subjects are allowed to eat freely, three times a day. After a baseline period of normal consumption, a dosage of glucose is administered with each meal, coated with either the rapidly dissolving or the slowly dissolving coating. Gastric emptying is monitored using standard techniques. The test takes as little as 2 weeks. Once confirmed, the desired satiety agent is similarly tested, replacing the glucose and using similar coatings.

STUDY 9

The proposed coating(s) are used to encapsulate the non-absorbable marker, polyethylene glycol 14C-PEG. 10% of the coated particles are overcoated with 113m-in-plexiglass and used to determine, with gamma scintigraphy, the rate of delivery of the drug particles to terminal ileum (previously outlined with 99m-Tc). Simultaneously, a double-lumen, marker-perfusion system in the ileum is used to determine the extent to which the 14C-PEG has been released from the other 90% of enterically coated particles. This study is carried out in a few weeks and is used repeatedly in different volunteers to test several different delivery vehicles.

STUDY 10

The product is tested in several ways. Because of CNS compensation, however, weight loss per se is not consistently achieved on a 40% reduction of intake of food alone. In a cross-over trial with limited numbers of normal or obese volunteers, it is tested against a placebo to determine whether it reduces food consumption. The agent is tested against placebo as an adjunct to sustain weight loss in obese subjects who have just completed a weight reduction program. And, it is tested against a placebo for inducing weight loss in obese subjects who are undergoing an exercise program.

DESCRIPTION OF THE PREFERRED EMBODIMENTS

The preferred enteric coating is a pH sensitive polymer that dissolves at the neutral to slightly alkaline pH of the human ileum (pH 7.5). A commonly used currently approved coating of this nature is Eudragit S, Rohm Pharma GmbH, Welsterstadt, Germany.

The use of a pH-sensitive coating has the advantage of targeting coating dissolution to the ileum, independent of transit time. Along the human GI tract, the stomach is very acidic (pH 1.5–4.5) and the proximal bowel is below neutral pH (pH 60.0–6.5); but the pH rises to a peak of 7.8 in the distal small intestine because of the increasing predominance of bicarbonate anion secretion by small intestinal mucosa into the lumen. Eudragit S is a weak acid polymer which is insoluble below pH 7 and thus tends to rupture in the ileum, where the contents of drug formulation would be disgorged. There are other forms of targeting to regions; for example, an enteric coating made of diazotized polymer may be solubilized as anaerobic bacteria in the terminal ileum and cecum, reduce and thus split the diazo bond. Nevertheless, the concentration of such bacteria in more proximal ileum is unknown, so a pH sensitive mechanism is preferred in the current context.

There are also enteric coatings, such as hydroxy cellulose, that rupture with time as they slowly hydrate and swell to bursting. It is common to achieve a 2–3 hour delay to burst with such materials. Nevertheless, it is desirable to have release specifically in the ileum, while being simultaneously free to adjust mouth to ileal transit by altering gastric residence time through particle diameter. Using a time dependent, rather than a site or pH dependent, mechanism impairs this freedom in the design of the dosage form.

Sodium dodecanoate or sodium dodecylsulfate are the preferred active ingredients. Since the availability of pancreatic enzymes to digest polymeric nutrients in the ileum is unpredictable, the nutrient should be in a predigested (monomeric) form. While it is known that glucose is very active in canine ileum at slowing gastric emptying and most likely is similarly active in the human ileum, acute experiments indicate that glucose is not a good satiety agent in the ileum, but that fat is. Furthermore, fatty acids, like dodecanoic acid, are much more slowly absorbed than glucose, so that even small amounts may achieve a long length of contact.

Since the preferred enteric coating is pH sensitive, its contents should re-enforce the pH of the lumen, rather than promote a different pH. For example, if small amounts of water leak through cracks into the coated sphere and hydrate the content, and alkaline pH on the interior surface of the coating may speed coating dissolution with premature rupture despite an acidic, luminal pH around the outside of the coating. Sodium dodecanoate, on dissolution in water, achieves a pH of about 80.0, whereas bicarbonate-rich ileal juice is at a pH of around 7.5. By contrast, sodium oleate achieves a pH around 9.5 and so may promote premature rupture of the coating even in the jejunum. Nevertheless, even sodium dodecanoate is a weak acid buffer and therefore may speed coating dissolution.

The other preferred active ingredient is sodium dodecylsulfate. This material is known to be biologically active—for example, when in the proximal intestinal lumen, it stimulates pancreatic secretion even better than dodecanoic acid—but since it is a stronger sulfonic, rather than a weaker carboxylic acid, it does not have the buffering effect that could lead to premature rupture of a pH sensitive coating. On the other hand, dodecanoate is a natural foodstuff, whereas dodecylsulfate is not, so that the commercial choice might be potentially influenced by FDA requirements for toxicity studies.

Sodium dodecanoate and sodium dodecylsulfate are much more readily soluble at luminal pH than sodium oleate. The dodecanoate does not require bile salt to emulsify it, whereas dispersion of sodium oleate would be aided by bile salt. Dispersion into solution is necessary for the nutrient to contact the sensory nerves in the intestinal mucosa.

The density of enteric-coated particles comprising the dosage form may be about 1.0 and the diameter about 2.0 mm. These may be ingested at mealtime as a slurry in a pleasant tasting but low calorie drink. The drink may have a pH of less than 6 and may be, for example, orange juice or coffee. The slurry and the drink may also be marketed together. The size and density are designed to place the dosage form in the ileum for maximum efficacy at the time of the next meal, 4–6 hours later. The slurry provides unconstrained ability to adjust the active dose.

Fatty acids have densities around 0.80 and sodium salts of fatty acids about 0.90. Enteric-coated particles made up of these substances, however, have a density close to 1.0 because of the weight of the enteric coating. It is known that particles less or more dense than 1.0 empty from the stomach more slowly than particles of the same diameter but a density of 1.0. Since the knowledge of human gastric emptying of spheres of different sizes is derived almost entirely from study of spheres with a density of 1.0, a particle with a density of 1.0 is desirable in order to predict its behavior. If the coated particles of sodium dodecanoate are significantly less dense than 1.0, the density of the particles may be increased by including an incipient, such as NaCl of trisodium citrate. Trisodium citrate buffers to pH 5 and thus may counteract the more alkaline buffering of the sodium dodecanoate.

A particle with a density of 1.0 and a diameter of 20.0 mm may have a gastric residence such that about half of the particles would empty from the stomach in 150 minutes after ingestion. It is known that postcibal transit from human pylorus to cecum averages 100–150 minutes. Thus median transit from mouth to mid ileum would be 200–250 minutes with this dosage form. This transit may place the bulk of the dosage in the ileum by the time of the next meal, 4–6 hours later. Since postcibal pylorus to cecum (i.e., small intestinal) transit time seems to be constant regardless of particle size, whereas the gastric residence can be shortened or lengthened by changing particle diameter, the time of arrival of the drug particles into ileum may be modified, as needed, by adjusting the size of the particles in the formulation.

It is now known from canine and human studies that while the half-time of gastric emptying of small particles is determined by particle diameter and density, the number of particles emptied per time varies directly with the number ingested, independent of meal size (i.e., of the amount of solid food ingested). Thus, the absolute amount of active ingredient arriving in the ileum 4–6 hours after ingestion may be regulated independently from the transit time of the particles by regulating the number of particles ingested in the slurry. Furthermore, the number of particles needed depends, as well, on the ratio of volumes of active ingredient to coating. The optimum dosage, therefore, can be achieved by adjusting the concentration (i.e., number of teaspoons of particles per glass of drink) or total amount of particles in the slurry.

The appetite control composition of the invention may be used as an adjunct to a weight loss program to reduce increased hunger or craving for food during the forced restriction in caloric intake. Alternatively, the composition of the invention may be used as a direct weight-loss-maintenance device, effective by virtue of the ability of the composition to reduce food intake by about 40%; or, the composition of the invention may be used as an adjunct to a restricted weight-loss-maintenance diet, effective by virtue of the ability of the composition to induce satiety.

The invention disclosed herein is not considered to be limited to the preferred embodiments. It is contemplated that any method for the control of appetite which includes selective delivery to the ileum of food grade nutrients, is within the scope of the invention.

TABLE 1

Amino Acids on Sham Feeding in Rats*

| Perfusate | ml Drunk/90 min |
|---|---|
| 0.15M NaCl: | 70 ± 11 |
| L-alanine: | 70 ± 13 |
| 0.15M NaCl: | 84 ± 12 |
| L-arginine: | 79 ± 8 |
| 0.15M NaCl: | 64 ± 13 |
| L-leuncine: | 39 ± 6 |
| 0.15M NaCl: | 55 ± 10 |
| L-tyrptophan: | 25 ± 7** |

*Responses are $\mu$ ± s.e, 7–8 rats. Amino acids were infused into duodenum at 2.88 moles/h, except for tryptophan which, because of low solubility, was infused at 1.44 mmoles/h.
**Despite this slower rate, only tryptophan significantly inhibited ($p < .05$) when compared to saline infusions.

TABLE 2

Fatty Acids on Sham Feeding in Rats*

| Perfusate | ml Drunk/90 min |
|---|---|
| 0.15M NaCl: | 66 ± 11 |
| 80 mM dodecanoate: | 27 ± 7** |
| 0.15M NaCl: | 62 ± 12 |
| 80 mM decanoate: | 75 ± 10 |
| 0.15M NaCl: | 68 ± 10 |
| 120 mM octanoate: | 72 ± 11 |

*Responses are $\mu$ ± s.e, 6–12 rats. All 3 fatty acid soaps were perfused into duodenum at 12 ml/h & above the critical micellar concentrations.
**Only dodecanoate inhibited significantly more than saline controls ($p < .005$). This specificity indicates a response specific to chemical structure, and not a non-specific response to detergency.

TABLE 3

Intestinal Distributions of Infused Dodecanoate on Satiety in Freely Feeding Rats

| Infusion Mode | mmoles/h | % Reduction | Reduction Ratio |
|---|---|---|---|
| 1) duodenum, 80 mM, @ 6 ml/h: | 0.48 | −4.2%* | 0.00 |
| 2) duodenum, 80 mM, @ 12 ml/h | 0.96 | 46.6 | 4.40 |
| 3) duodenum, 80 mM, @ 6 ml/h + midgut, 80 mM, @ 6 ml/h | 0.96 | 68.3 | 6.82 |
| 4) duodenum, 80 mM, @ 6 ml/h + midgut, 80 mM, @ 4 ml/h | 0.8 | 51.8 | 6.19 |
| 5) midgut, 80 mM, @ 12 ml/h | 0.96 | 46.3 | 4.37 |
| 6) midgut, 80 mM, @ 6 ml/h: | 0.48 | 21.7 | 4.11 |

*This response was not significantly different from zero; i.e., no reduction of food intake was achieved.

I claim:

1. A composition comprising a pharmaceutically acceptable satiety agent comprising an active ingredient selected from the group consisting of sodium dodecanoate, sodium dodecylsulfate and mixtures thereof, and a pharmaceutically acceptable delivery agent, formulated for predominant release of the satiety agent in the ileum.

2. A composition according to claim 1 wherein the pharmaceutically acceptable delivery agent is selected from the group consisting of ion exchange resins and enteric coatings.

3. A composition according to claim 2 wherein the delivery agent is an ion exchange resin.

4. A composition according to claim 2 wherein the delivery agent is an enteric coating.

5. A composition according to claim 4 wherein the enteric coating is selected from the group consisting of pH sensitive polymers, diazotized polymers, and cellulosic polymers.

6. A composition according to claim 5 wherein the enteric coating is selected from the group consisting of pH sensitive polymers.

7. An appetite control composition comprising:

a satiety agent comprising an active ingredient selected from the group consisting of sodium dodecanoate, sodium dodecylsulfate and mixtures thereof, and a delivery agent selected from the group consisting of ion exchange resins, pH sensitive polymers, diazotized polymers, and cellulosic polymers.

8. An appetite control composition according to claim 7 wherein the delivery agent is selected from the group consisting of pH sensitive polymers.

9. An appetite control composition according to claim 7, wherein said composition is formulated in the form of particles, and said particles are between 1 and 3 millimeters in diameter.

10. An appetite control composition according to claim 9 wherein the particles have a density between 0.5 and 20.0.

11. An appetite control composition according to claim 10, wherein the particles have a density between 0.75 and 1.25.

* * * * *